US011421213B2

(12) United States Patent
Fernandez et al.

(10) Patent No.: US 11,421,213 B2
(45) Date of Patent: *Aug. 23, 2022

(54) PERFORMANCE-ENHANCED PROTEASE VARIANTS II

(71) Applicant: Henkel AG & Co. KGaA, Duesseldorf (DE)

(72) Inventors: Layla Fernandez, Cologne (DE); Sabine Griemert, Monheim am Rhein (DE); Nina Mussmann, Willich (DE); Susanne Wieland, Dormagen/Zons (DE); Daniela Herbst, Duesseldorf (DE); Inken Prueser, Duesseldorf (DE); Christian Degering, Erkrath (DE); Daria Strauss, Duesseldorf (DE); Thorsten Eggert, Hattingen (DE); Christian Leggewie, Muelheim an der Ruhr (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/644,191

(22) PCT Filed: Sep. 5, 2018

(86) PCT No.: PCT/EP2018/073880
§ 371 (c)(1),
(2) Date: Mar. 4, 2020

(87) PCT Pub. No.: WO2019/048486
PCT Pub. Date: Mar. 14, 2019

(65) Prior Publication Data
US 2020/0231957 A1     Jul. 23, 2020

(30) Foreign Application Priority Data

Sep. 5, 2017  (DE) .................... 10 2017 215 631.7
Jun. 5, 2018  (DE) .................... 10 2018 208 777.6

(51) Int. Cl.
*C12N 9/54*   (2006.01)
*C11D 3/386*  (2006.01)

(52) U.S. Cl.
CPC ............. *C12N 9/54* (2013.01); *C11D 3/386* (2013.01); *C12Y 304/21062* (2013.01)

(58) Field of Classification Search
CPC .................. C12N 9/54; C11D 3/386
See application file for complete search history.

(56) References Cited

U.S. PATENT DOCUMENTS

| 10,920,258 B2* | 2/2021 | Nuijens | ............... C12P 21/02 |
| 2009/0170745 A1* | 7/2009 | Merkel | .................. C11D 3/386 510/320 |
| 2014/0038876 A1* | 2/2014 | Ostergaard | ......... C11D 3/38681 510/392 |

FOREIGN PATENT DOCUMENTS

| WO | 2007131656 A1 | 11/2007 |
| WO | 2009121725 A1 | 10/2009 |
| WO | 2011036263 A1 | 3/2011 |
| WO | 2017162429 A1 | 9/2017 |
| WO | 2017198488 A1 | 11/2017 |

OTHER PUBLICATIONS

Okshevsky et al., Uniprot database search, acession No. A0A1J5XCS3, Feb. 2017.*
Okshevsky et al., UniProt database, accession No. A0A1J5XCS3, Feb. 2017.*
"RecName: Full=Subtilisin Carlsberg; EC=3.4.21.62; Flags: Precursor", UNIPROT, Jul. 21, 1986, 3 pages.
Bryan, "Protein engineering of subtilisin", Biochimica et Biophysica Acta, 2000, pp. 203-222, vol. 1543, Issue 2.
Von Der Osten et al., "Protein engineering of subtilisins to improve stability in detergent formulations", Journal of Biotechnology, 1993, pp. 55-68, vol. 28, Issue 1.
Vojcic et al., "Advances in protease engineering for laundry detergents", New Biotechnology, 2015, pp. 629-634, vol. 32, No. 6.
International search report from parallel PCT Patent Application PCT/EP2018/073880 dated Nov. 8, 2018, 12 pages (for reference purposes only).

* cited by examiner

*Primary Examiner* — Maryam Monshipouri
(74) *Attorney, Agent, or Firm* — Viering Jentschura & Partner MBB

(57) ABSTRACT

An amino acid sequence may have at least 70% sequence identity to the amino acid sequence identified in SEQ ID No. 1 over its entire length, and (a) amino acid substitutions at the positions corresponding to the positions 9 and 271 in each case based on the numbering according to SEQ ID No. 1, and (b) an amino acid substitution on at least one of the positions corresponding to the positions 29, 48, 101, 30, 131, 133, 144, 224 or 252, in each case based on the numbering according to SEQ ID No. 1. Such proteases are particularly suitable for having an improved cleaning performance.

15 Claims, No Drawings
Specification includes a Sequence Listing.

PERFORMANCE-ENHANCED PROTEASE VARIANTS II

CROSS-REFERENCE TO RELATED APPLICATIONS

The present application is a national stage entry according to 35 U.S.C. § 371 of PCT application No.: PCT/EP2018/073880 filed on Sep. 5, 2018; which claims priority to German application No.: 10 2017 215 631.7 filed on Sep. 5, 2017, as well as claims priority to German application No.: 10 2018 208 777.6 filed on Jun. 5, 2018; all of which are incorporated herein by reference in their entirety and for all purposes.

REFERENCE TO A SEQUENCE LISTING SUBMITTED VIA EFS-WEB

The content of the ASCII text file of the sequence listing named "P75336US_sequencelisting_ST25" which is 58 kb in size was created on Sep. 5, 2017 and electronically submitted via EFS-Web herewith. The sequence listing is incorporated herein by reference in its entirety.

TECHNICAL FIELD

Proteases from *Bacillus pumilus*, the amino acid sequences of which have been altered to give them a better storage stability, in particular with regard to the use in washing and cleaning agents, and also relates to the nucleic acids coding for said proteases and to the production thereof.

BACKGROUND

Proteases are some of the technically most important enzymes. They are the longest established enzymes for washing and cleaning agents, and are contained in virtually all modern, effective washing and cleaning agents. They bring about the decomposition of protein-containing stains on the item to be cleaned. Of these, in turn, proteases of the subtilisin type (subtilases, subtilopeptidases, EC 3.4.21.62) are particularly important, which are serine proteases due to the catalytically active amino acids. They act as non-specific endopeptidases and hydrolyze any acid amide bonds that are inside peptides or proteins. Their optimum pH is usually in the distinctly alkaline range. The article "Subtilases: Subtilisin-like Proteases" by R. Siezen, pages 75-95 in "Subtilisin enzymes," published by R. Bott and C. Betzel, New York, 1996, gives an overview of this family, for example. Subtilases are naturally formed from microorganisms. In particular, the subtilisins formed and secreted by *Bacillus* species are the most significant group of subtilases.

Examples of the subtilisin proteases used in washing and cleaning agents are the subtilisins BPN' and Carlsberg, the protease PB92, the subtilisins 147 and 309, the protease from *Bacillus lentus*, in particular from *Bacillus lentus* DSM 5483, subtilisin DY and the enzymes thermitase, proteinase K and the proteases TW3 and TW7, which can be classified as subtilases but no longer as subtilisins in the narrower sense, and variants of said proteases having an amino acid sequence that has been altered with respect to the starting protease. Proteases are altered in a targeted manner or randomly using methods known from the prior art, and are thus optimized for use in washing and cleaning agents, for example. This includes point, deletion or insertion mutagenesis, or fusion with other proteins or protein parts. Appropriately optimized variants are therefore known for the majority of proteases known from the prior art.

European patent application EP2016175A1 discloses, for example, a protease from *Bacillus pumilus* intended for washing and cleaning agents. In general, only selected proteases are suitable for use in liquid, surfactant-containing preparations in any case. Many proteases do not exhibit sufficient catalytic performance in such preparations. For the use of proteases in cleaning agents, therefore, a high catalytic activity under conditions as they are during a wash cycle and a high storage stability is particularly desirable.

Consequently, protease and surfactant-containing liquid formulations from the prior art are disadvantageous in that the proteases contained, under standard washing conditions (e.g. in a temperature range of from 20° C. to 40° C.), do not have satisfactory proteolytic activity or are not storage-stable and the formulations therefore do not exhibit optimal cleaning performance on protease-sensitive stains.

SUMMARY

Surprisingly, it has now been found that a protease from *Bacillus pumilus* or a sufficiently similar protease (based on the sequence identity) that has amino acid substitutions (a) at the positions corresponding to positions 9 and 271, in each case based on the numbering according to SEQ ID NO:1, and (b) at at least one of the positions corresponding to positions 29, 48, 101, 130, 131, 133, 144, 224 or 252, in each case based on the numbering according to SEQ ID NO:1, is improved in terms of storage stability compared with the wild-type form and/or reference mutants and is therefore particularly suitable for use in washing or cleaning agents.

In a first aspect, a protease may include an amino acid sequence which has at least 70% sequence identity with the amino acid sequence given in SEQ ID NO:1 over its entire length and (i) has amino acid substitutions, such as the amino acid substitutions 9T, 9H, 9S or 9A and 271E, at the positions corresponding to positions 9 and 271 according to SEQ ID NO:1, and (ii) has an amino acid substitution at at least one of the positions corresponding to positions 29, 48, 101, 130, 131, 133, 144, 224 or 252, in each case based on the numbering according to SEQ ID NO:1.

In one embodiment of this first aspect, a protease may include an amino acid sequence which has at least 70% sequence identity with the amino acid sequence given in SEQ ID NO:1 over its entire length and has, in each case based on the numbering according to SEQ ID NO:1:
   (a) amino acid substitutions, in particular the amino acid substitutions 9T, 130D, 144K, 252T and 271E, at the positions corresponding to positions 9, 130, 144, 252 and 271; as well as optionally
   (b1) the amino acid substitution 166M, 166Q or 166A at the position corresponding to position 166; and/or
   (b2) at least one further amino acid substitution at at least one of the positions corresponding to positions 62, 133, 149, 156, 172 or 217.

In a second aspect, a protease may include an amino acid sequence which has at least 70% sequence identity with the amino acid sequence given in SEQ ID NO:1 over its entire length and, based on the numbering according to SEQ ID NO:1, has at least one amino acid substitution at at least one of the positions corresponding to positions 62, 149, 156, 166, 172 or 217, the amino acid substitution at the position corresponding to position 166 being selected from 166M, 166Q and 166A, and the amino acid substitution at the position corresponding to position 62 being selected from 62S.

In a further aspect, a protease may have an amino acid sequence which has at least 70% sequence identity with the amino acid sequence given in SEQ ID NO:1 over its entire length and which comprises at least one amino acid substitution selected from the group consisting of N130D, N130S, N130H, G131N, G131D, G131K, T133K, T133Y, N144L, N144A, S224A, or N252S, in each case based on the numbering according to SEQ ID NO:1. In such an embodiment, the protease has either no substitutions at positions 9 and 271, and optionally also no substitution at position 216, or it has a substitution at one of positions 9 and 271, and optionally also a substitution at position 216.

In various embodiments of the aspects described above, the sequence identity with SEQ ID NO:1 may be 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, or 98.8%.

A method for producing a protease, may include the substitution of amino acids in a starting protease which has at least 70% sequence identity with the amino acid sequence given in SEQ ID NO:1 over its entire length (i) at the positions corresponding to positions 9 and 271 in SEQ ID NO:1, such that the protease comprises the amino acid substitutions 9T, 9H, 9S or 9A, in particular 9T and 271E, at the positions, and (ii) at at least one position corresponding to position 29, 48, 101, 130, 131, 133, 144, 224 or 252 in SEQ ID NO:1, such that the protease has at least one of the amino acid substitutions 29G, 48V, 101E, 130D, 130S, 130H, 131S, 131N, 131D, 131K, 133K, 133R, 133Y, 144K, 144L, 144A, 224A, 224T, 252T or 252S. The protease that can be obtained by this method has at least 70% sequence identity with the amino acid sequence given in SEQ ID NO:1 over its entire length.

In various embodiments of this aspect, a method for producing a protease as defined above, may include the substitution of amino acids in a starting protease which has at least 70% sequence identity with the amino acid sequence given in SEQ ID NO:1 over its entire length (i) at the positions corresponding to positions 9, 130, 144, 252 and 271 in SEQ ID NO:1, such that the protease comprises amino acid substitutions, in particular the amino acid substitutions 9T, 130D, 144K, 252T and 271E, at the positions, and optionally (ii) at the position corresponding to position 166 in SEQ ID NO:1, such that the protease has at least one of the amino acid substitutions 166M, 166Q or 166A and/or (iii) has at least one further amino acid substitution at at least one of the positions corresponding to positions 62, 133, 149, 156, 172 or 217 in SEQ ID NO:1. The protease that can be obtained by this method has at least 70% sequence identity with the amino acid sequence given in SEQ ID NO:1 over its entire length.

DETAILED DESCRIPTION

A protease within the meaning of the present patent application therefore comprises both the protease as such and a protease produced by a method. All statements regarding the protease therefore relate both to the protease as such and to the proteases produced by means of corresponding methods.

Further aspects relate to the nucleic acids coding for these proteases, to non-human host cells containing proteases or nucleic acids, and to agents comprising proteases, in particular washing and cleaning agents, to washing and cleaning methods, and to uses of the proteases in washing or cleaning agents in order to remove protein-containing stains.

"At least one," as used herein, means one or more, i.e. 1, 2, 3, 4, 5, 6, 7, 8, 9, 10, 11, 12, 13, 14 or more.

When the protease is defined herein such that it includes "the amino acid substitutions 9T, 9H, 9S or 9A," this means that position 9 is mutated to either T, H, S or A. Thus, the phrase whereby the protease comprises "the amino acid substitutions 9T, 9H, 9S or 9A and 271E and optionally 216C" means that position 9 is mutated to either T, H, S or A, position 271 is mutated to E and position 216 is optionally mutated to C.

A surprising finding by the inventors relates to amino acid substitutions at the positions corresponding to positions 9 and 271, in each case based on the numbering according to SEQ ID NO:1, such that the protease comprises the amino acid substitutions 9T, 9H, 9S or 9A and 271E at the positions, and an amino acid substitution at at least one of the positions corresponding to positions 29, 48, 101, 130, 131, 133, 144, 224 or 252 of the protease from *Bacillus pumilus* according to SEQ ID NO:1, in a protease comprising an amino acid sequence that is at least 70% identical to the amino acid sequence given in SEQ ID NO:1, such that the amino acids 29G, 48V, 101E, 130D, 130S, 130H, 131S, 131N, 131D, 131K, 133K, 133R, 133Y, 144K, 144L, 144A, 224A, 224T, 252T or 252S are present at at least one of the corresponding positions, results in improved storage stability of this altered protease in washing and cleaning agents. It has further been found that this storage stability in proteases based on the sequence according to SEQ ID NO:1, which have amino acid substitutions, in particular the amino acid substitutions 9T, 130D, 144K, 252T and 271E, at the positions corresponding to positions 9, 130, 144, 252 and 271; and optionally (b1) have the amino acid substitutions 166M, 166Q or 166A at the position corresponding to position 166; and/or (b2) have at least one further amino acid substitution at at least one of the positions corresponding to positions 62, 133, 149, 156, 172 or 217, is improved in a particularly advantageous manner. This is particularly surprising insofar as none of the above-mentioned amino acid substitutions has previously been associated with increased storage stability of the protease. Optionally, improved performance of this altered protease (proteolytic activity under standard washing conditions) can additionally be brought about in washing and cleaning agents.

In various embodiments of the protease, the protease has amino acid substitutions (A) (i) at the positions corresponding to positions 9, 131 and 271, in each case based on the numbering according to SEQ ID NO:1, and optionally (ii) at at least one of the positions corresponding to positions 29, 48, 101, 130, 133, 144, 224 or 252, in each based on the numbering according to SEQ ID NO:1;

(B) (i) at the positions corresponding to positions 9, 133 and 271, in each case based on the numbering according to SEQ ID NO:1, and optionally (ii) at at least one of the positions corresponding to positions 29, 48, 101, 130, 131, 144, 224 or 252, in each based on the numbering according to SEQ ID NO:1;

(c) (i) at the positions corresponding to positions 9, 224 and 271, in each case based on the numbering according to SEQ ID NO:1, and optionally (ii) at at least one of the positions corresponding to positions 29, 48, 101, 130, 131, 133, 144 or 252, in each based on the numbering according to SEQ ID NO:1;

(D) (i) at the positions corresponding to positions 9, 130 and 271, in each case based on the numbering according to SEQ ID NO:1, and optionally (ii) at at least one of the positions corresponding to positions 29, 48, 101, 131, 133, 144, 224 or 252, in each based on the numbering according to SEQ ID NO:1; or
- (E) (i) at the positions corresponding to positions 9, 144 and 271, in each case based on the numbering according to SEQ ID NO:1, and optionally (ii) at at least one of the positions corresponding to positions 29, 48, 101, 130, 131, 133, 224 or 252, in each based on the numbering according to SEQ ID NO:1;
- (F) (i) at the positions corresponding to positions 9, 252 and 271, in each case based on the numbering according to SEQ ID NO:1, and optionally (ii) at at least one of the positions corresponding to positions 29, 48, 101, 130, 131, 133, 144 or 224, in each based on the numbering according to SEQ ID NO:1;
- (G) (i) at the positions corresponding to positions 9, 130, 133 and 271, in each case based on the numbering according to SEQ ID NO:1, and optionally (ii) at at least one of the positions corresponding to positions 29, 48, 101, 131, 144, 224 or 252, in each based on the numbering according to SEQ ID NO:1;
- (H) (i) at the positions corresponding to positions 9, 130, 144 and 271, in each case based on the numbering according to SEQ ID NO:1, and optionally (ii) at at least one of the positions corresponding to positions 29, 48, 101, 131, 133, 224 or 252, in each based on the numbering according to SEQ ID NO:1;
- (0) (i) at the positions corresponding to positions 9, 130, 252 and 271, in each case based on the numbering according to SEQ ID NO:1, and optionally (ii) at at least one of the positions corresponding to positions 29, 48, 101, 131, 133, 144 or 224, in each based on the numbering according to SEQ ID NO:1;
- (J) (i) at the positions corresponding to positions 9, 133, 144 and 271, in each case based on the numbering according to SEQ ID NO:1, and optionally (ii) at at least one of the positions corresponding to positions 29, 48, 101, 130, 131, 224 or 252, in each based on the numbering according to SEQ ID NO:1;
- (K) (i) at the positions corresponding to positions 9, 133, 252 and 271, in each case based on the numbering according to SEQ ID NO:1, and optionally (ii) at at least one of the positions corresponding to positions 29, 48, 101, 130, 131, 144 or 224, in each based on the numbering according to SEQ ID NO:1;
- (L) (i) at the positions corresponding to positions 9, 144, 252 and 271, in each case based on the numbering according to SEQ ID NO:1, and optionally (ii) at at least one of the positions corresponding to positions 29, 48, 101, 130, 131, 133 or 224, in each based on the numbering according to SEQ ID NO:1;
- (M) (i) at the positions corresponding to positions 9, 130, 144, 252 and 271, in each case based on the numbering according to SEQ ID NO:1, and optionally (ii) at at least one of the positions corresponding to positions 29, 48, 101, 131, 133 or 224, in each based on the numbering according to SEQ ID NO:1;
- (N) (i) at the positions corresponding to positions 9, 133, 144, 252 and 271, in each case based on the numbering according to SEQ ID NO:1, and optionally (ii) at at least one of the positions corresponding to positions 29, 48, 101, 130, 131 or 224, in each based on the numbering according to SEQ ID NO:1;
- (O) (i) at the positions corresponding to positions 9, 130, 133, 252 and 271, in each case based on the numbering according to SEQ ID NO:1, and optionally (ii) at at least one of the positions corresponding to positions 29, 48, 101, 131, 144 or 224, in each based on the numbering according to SEQ ID NO:1;
- (P) (i) at the positions corresponding to positions 9, 130, 133, 144 and 271, in each case based on the numbering according to SEQ ID NO:1, and optionally (ii) at at least one of the positions corresponding to positions 29, 48, 101, 131, 224 or 252, in each based on the numbering according to SEQ ID NO:1;
- (Q) (i) at the positions corresponding to positions 9, 130, 133, 144, 252 and 271, in each case based on the numbering according to SEQ ID NO:1, and optionally (ii) at at least one of the positions corresponding to positions 29, 48, 101, 131 or 224, in each based on the numbering according to SEQ ID NO:1; or
- (R) (i) has amino acid substitutions, in particular the amino acid substitutions 9T, 130D, 144K, 252T and 271E, at the positions corresponding to positions 9, 130, 144, 252 and 271; and (ii) has one of the amino acid substitutions 62S, 149I, 156G, 156Q, 166M, 166Q, 166A, 172P, 172G or 217M at one of the positions corresponding to positions 62, 149, 156, 166, 172 or 217.

In further embodiments, proteases are those having amino acid substitutions at the positions:

9 and 271 and at least one of 131, 133, 224, 130 and 144, and optionally at least one of 29, 48, 101 and 252;

9+271+131+224 and optionally at least one of 29, 48, 101, 130, 133, 144 or 252;

9+271+131+130 and optionally at least one of 29, 48, 101, 130, 144, 224 or 252;

9+271+131+130+224 and optionally at least one of 29, 48, 101, 130, 144 or 252; or 9+271+131+133+224+130 and optionally at least one of 29, 48, 101, 144 or 252;

Here, the corresponding exchanges are in particular those mentioned above, i.e. 9T, 9H, 9S, 9A, 29G, 48V, 101E, 130D, 130S, 130H, 131D, 131N, 131S, 131K, 133K, 133R, 133Y, 144K, 144L, 144A, 224A, 224T, 252S, 252T and/or 271E.

In various embodiments, the protease has
(1) amino acid substitutions, in particular the amino acid substitutions 9T, 130D, 144K, 252T and 271E, at the positions corresponding to positions 9, 130, 144, 252 and 271; and
(2) one of the amino acid substitutions 62S, 149I, 156G, 156Q, 166M, 166Q, 166A, 172P, 172G or 217M at one of the positions corresponding to positions 62, 149, 156, 166, 172 or 217;

In embodiments of the protease, the protease has substitutions selected from the amino acid substitutions 149I, 156G, 156Q, 172P, 172G and 217M at the positions corresponding to positions 149, 156, 172 or 217.

In various embodiments, the protease has amino acid substitutions, in particular the amino acid substitutions 9T, 130D, 144K, 252T and 271E, at the positions corresponding to positions 9, 130, 144, 252 and 271; and has at least one, for example 1, 2, 3, 4, 5 or 6, for example 1, 2, 3 or 4, further amino acid substitutions at one or more of the positions corresponding to positions 62, 149, 156, 166, 172 or 217, these being selected from: 62S, 149I, 156G, 156Q, 166M, 166Q, 166A, 172P, 172G or 217M. Such proteases are disclosed for example as mutants 7-12 in example. Particularly suitable are those proteases which have an amino acid substitution, in particular the amino acid substitution 271E, at the position corresponding to position 271; and have the amino acid substitutions 9T, 130D, 144K and 252T at the positions corresponding to positions 9, 130, 144 and 252;

and at least one, for example 1, 2 or 3, further amino acid substitution(s) at one or more of the positions corresponding to positions 62, 166 or 217, these being selected from: 62S, 166Q and 217M.

In further embodiments, the protease has amino acid substitutions at the positions (in the numbering according to SEQ ID NO:1):
9+271+29
9+271+48
9+271+101
9+271+130
9+271+131
9+271+133
9+271+144
9+271+224
9+271+252
9+271+29+48
9+271+29+101
9+271+29+130
9+271+29+131
9+271+29+133
9+271+29+144
9+271+29+224
9+271+29+252
9+271+48+101
9+271+48+130
9+271+48+131
9+271+48+133
9+271+48+144
9+271+48+224
9+271+48+252
9+271+101+130
9+271+101+131
9+271+101+133
9+271+101+144
9+271+101+224
9+271+101+252
9+271+130+131
9+271+130+133
9+271+130+144
9+271+130+224
9+271+130+252
9+271+131+133
9+271+131+144
9+271+131+224
9+271+131+252
9+271+133+144
9+271+133+224
9+271+133+252
9+271+144+224
9+271+144+252
9+271+224+252
9+271+29+48+101
9+271+29+48+130
9+271+29+48+131
9+271+29+48+133
9+271+29+48+144
9+271+29+48+224
9+271+29+48+252
9+271+29+101+130
9+271+29+101+131
9+271+29+101+133
9+271+29+101+144
9+271+29+101+224
9+271+29+101+252
9+271+29+130+131
9+271+29+130+133
9+271+29+130+144
9+271+29+130+224
9+271+29+130+252
9+271+29+131+133
9+271+29+131+144
9+271+29+131+224
9+271+29+131+252
9+271+29+133+144
9+271+29+133+224
9+271+29+133+252
9+271+29+144+224
9+271+29+144+252
9+271+29+224+252
9+271+48+101+130
9+271+48+101+131
9+271+48+101+133
9+271+48+101+144
9+271+48+101+224
9+271+48+101+252
9+271+48+130+131
9+271+48+130+133
9+271+48+130+144
9+271+48+130+224
9+271+48+130+252
9+271+48+131+133
9+271+48+131+144
9+271+48+131+224
9+271+48+131+252
9+271+48+133+144
9+271+48+133+224
9+271+48+133+252
9+271+48+144+224
9+271+48+144+252
9+271+48+224+252
9+271+101+130+131
9+271+101+130+133
9+271+101+130+144
9+271+101+130+224
9+271+101+130+252
9+271+101+131+133
9+271+101+131+144
9+271+101+131+224
9+271+101+131+252
9+271+101+133+144
9+271+101+133+224
9+271+101+133+252
9+271+101+144+224
9+271+101+144+252
9+271+101+224+252
9+271+130+131+133
9+271+130+131+144
9+271+130+131+224
9+271+130+131+252
9+271+130+133+144
9+271+130+133+224
9+271+130+133+252
9+271+130+144+224
9+271+130+144+252
9+271+130+224+252
9+271+131+133+144
9+271+131+133+224
9+271+131+133+252
9+271+131+144+224
9+271+131+144+252
9+271+131+224+252
9+271+133+144+224
9+271+133+144+252

9+271+133+224+252
9+271+144+224+252
9+271+29+48+101+130
9+271+29+48+101+131
9+271+29+48+101+133
9+271+29+48+101+144
9+271+29+48+101+224
9+271+29+48+101+252
9+271+29+48+130+131
9+271+29+48+130+133
9+271+29+48+130+144
9+271+29+48+130+224
9+271+29+48+130+252
9+271+29+48+131+133
9+271+29+48+131+144
9+271+29+48+131+224
9+271+29+48+131+252
9+271+29+48+133+144
9+271+29+48+133+224
9+271+29+48+133+252
9+271+29+101+130+131
9+271+29+101+130+133
9+271+29+101+130+144
9+271+29+101+130+224
9+271+29+101+130+252
9+271+29+101+131+133
9+271+29+101+131+144
9+271+29+101+131+224
9+271+29+101+131+252
9+271+29+101+133+144
9+271+29+101+133+224
9+271+29+101+133+252
9+271+29+101+144+224
9+271+29+101+144+252
9+271+29+101+224+252
9+271+29+130+131+133
9+271+29+130+131+144
9+271+29+130+131+224
9+271+29+130+131+252
9+271+29+130+133+144
9+271+29+130+133+224
9+271+29+130+133+252
9+271+29+130+144+224
9+271+29+130+144+252
9+271+29+130+224+252
9+271+29+131+133+144
9+271+29+131+133+224
9+271+29+131+133+252
9+271+29+131+144+224
9+271+29+131+144+252
9+271+29+131+224+252
9+271+29+133+144+224
9+271+29+133+144+252
9+271+29+133+224+252
9+271+29+144+224+252
9+271+48+101+130+131
9+271+48+101+130+133
9+271+48+101+130+144
9+271+48+101+130+224
9+271+48+101+130+252
9+271+48+101+131+133
9+271+48+101+131+144
9+271+48+101+131+224
9+271+48+101+131+252
9+271+48+101+133+144
9+271+48+101+133+224
9+271+48+101+133+252
9+271+48+101+144+224
9+271+48+101+144+252
9+271+48+101+224+252
9+271+48+130+131+133
9+271+48+130+131+144
9+271+48+130+131+224
9+271+48+130+131+252
9+271+48+130+133+144
9+271+48+130+133+224
9+271+48+130+133+252
9+271+48+130+144+224
9+271+48+130+144+252
9+271+48+130+224+252
9+271+48+131+133+144
9+271+48+131+133+224
9+271+48+131+133+252
9+271+48+131+144+224
9+271+48+131+144+252
9+271+48+131+224+252
9+271+48+133+144+224
9+271+48+133+144+252
9+271+48+133+224+252
9+271+48+144+224+252
9+271+101+130+131+133
9+271+101+130+131+144
9+271+101+130+131+224
9+271+101+130+131+252
9+271+101+130+133+144
9+271+101+130+133+224
9+271+101+130+133+252
9+271+101+130+144+224
9+271+101+130+144+252
9+271+101+130+224+252
9+271+101+131+133+144
9+271+101+131+133+224
9+271+101+131+133+252
9+271+101+131+144+224
9+271+101+131+144+252
9+271+101+131+224+252
9+271+101+133+144+224
9+271+101+133+144+252
9+271+101+133+224+252
9+271+101+144+224+252
9+271+130+131+133+144
9+271+130+131+133+224
9+271+130+131+133+252
9+271+130+131+144+224
9+271+130+131+144+252
9+271+130+131+224+252
9+271+130+133+144+224
9+271+130+133+144+252
9+271+130+133+224+252
9+271+130+144+224+252
9+271+131+133+144+224
9+271+131+133+144+252
9+271+131+133+224+252
9+271+131+144+224+252
9+271+133+144+224+252

In various embodiments, the aforementioned variants do not have further substitutions or have only one or more additional substitutions in the positions from the group of positions of 29, 48, 101, 130, 131, 133, 144, 224 and 252, if these have not yet been mentioned above. In further embodiments, in particular in all the embodiments described above, the protease has at least one, for example 1, 2 or 3, additional amino acid substitutions at the positions corresponding to positions 62, 166 or 217, based on the numbering according to SEQ ID NO:1. In various embodiments, this additional amino acid substitution is a substitution at position 217. In various other embodiments, this additional substitution is one at position 62 and/or 166. The above-described amino acid substitution may be selected from: 62S, 166Q and 217M.

Further embodiments relate to protease variants which have amino acid substitutions at the following positions (in the numbering according to SEQ ID NO:1):
9+130+144+252+271+62
9+130+144+252+271+149
9+130+144+252+271+156
9+130+144+252+271+166
9+130+144+252+271+172
9+130+144+252+271+217
9+130+144+252+271+62+149
9+130+144+252+271+62+156
9+130+144+252+271+62+166
9+130+144+252+271+62+172
9+130+144+252+271+62+217
9+130+144+252+271+149+156
9+130+144+252+271+149+166
9+130+144+252+271+149+172
9+130+144+252+271+149+217
9+130+144+252+271+156+166
9+130+144+252+271+156+172
9+130+144+252+271+156+217
9+130+144+252+271+166+172
9+130+144+252+271+166+217
9+130+144+252+271+172+217
9+130+133+144+252+271+62
9+130+133+144+252+271+149
9+130+133+144+252+271+156
9+130+133+144+252+271+166
9+130+133+144+252+271+172
9+130+133+144+252+271+217
9+130+133+144+252+271+62+149
9+130+133+144+252+271+62+156
9+130+133+144+252+271+62+166
9+130+133+144+252+271+62+172
9+130+133+144+252+271+62+217
9+130+133+144+252+271+149+156
9+130+133+144+252+271+149+166
9+130+133+144+252+271+149+172
9+130+133+144+252+271+149+217
9+130+133+144+252+271+156+166
9+130+133+144+252+271+156+172
9+130+133+144+252+271+156+217
9+130+133+144+252+271+166+172
9+130+133+144+252+271+166+217
9+130+133+144+252+271+172+217

In various embodiments, the aforementioned variants do not have further substitutions or have only one or more additional substitutions in the positions from the group of positions of 62, 133, 149, 156, 166, 172 and 217, if these have not yet been mentioned above.

In all the aforementioned variants, the corresponding exchanges are in particular those mentioned above, i.e. 9T, 9H, 9S, 9A, 29G, 48V, 101E, 130D, 130S, 130H, 131D, 131N, 131S, 131K, 133K, 133R, 133Y, 144K, 144L, 144A, 224A, 224T, 252S, 252T and/or 271E. 9T, 130D, 133R/K, 144K, 252T/S and/or 271E, in particular 9T, 130D, 133R/K, 144K, 252T and 271E or 9T, 130D, 133K, 144K, 252T and 271E, are particularly suitable. A variant which has the substitutions 9T, 130D, 144K, 252T and 271E, and optionally also 133R/K and/or 217M, is further possible.

In embodiments of the protease, i.e. in particular the variants listed above, the protease has amino acid substitutions at the positions corresponding to positions 62, 149, 156, 166, 172 and 217, these being selected from: 62S, 149I, 156G, 156Q, 166M, 166Q, 166A, 172P, 172G or 217M.

Such proteases are disclosed for example as mutants in example 1. Particularly suitable are those proteases which have an amino acid substitution, in particular the amino acid substitution 271E, at the position corresponding to position 271; and have the amino acid substitutions 9T, 130D, 144K and 252T at the positions corresponding to positions 9, 130, 144 and 252; and at least one, for example 1, 2 or 3, further amino acid substitution(s) at one or more of the positions corresponding to positions 62, 166 or 217, these being selected from: 62S, 166Q and 217M.

In further embodiments, in particular in all the embodiments described above, the protease has an additional amino acid substitution at the position corresponding to position 216, based on the numbering according to SEQ ID NO:1. This amino acid substitution may be the amino acid substitution S216C. In various embodiments, however, the application described herein also relates to protease variants which do not have the substitution 216C, in particular do not have a substitution in the position 216 in the numbering according to SEQ ID NO:1.

Furthermore, in various embodiments, the protease contains at least one amino acid substitution selected from the group consisting of A29G, A48V, D101E, N130D, N130S, N130H, G131S, G131N, G131D, G131K, T133K, T133R, T133Y, N144K, N144L, N144A, S224A, S224T or N252S, in each case based on the numbering according to SEQ ID NO:1. In yet further embodiments, the protease contains the amino acid substitutions (1) P9T, P9H, P9S or P9A and (2) Q271E and optionally also (3) S216C and additionally one of the following amino acid substitution variants: (i) N130D, G131S, T133Y and S224A; (ii) N130S, G131S, T133Y, N144L and S224A; (iii) N130D, G131N, T133K and N144K; (iv) N130H, G131N, N144K and S224A; (v) A29G, N130D, G131N and T133R; (vi) A29G, D101E, N130S, G131S, S224T and N252S; (vii) N130H, G131S and S224A; (viii) N130D, G131S, T133K and S224A; (ix) A29G, D101E, N130D, G131K and S224A; (x) N130D, G131N T133K, N144L and N252S; (xi) G131S, N144K and S224T; (xii) D101E, N130D, G131S, T133Y, N144A and S224A; (xiii) A29G, D101E, N130S, S224T and N252S; (xiv) A48V, G131S, T133R and S224A; or (xv) G131D, T133R and S224A, the numbering being based in each case on the numbering according to SEQ ID NO:1.

In a further embodiment, the protease has an amino acid sequence according to SEQ ID Nos. 3-17 or 19-23 or 20-23.

The proteases have improved storage stability. They have increased stability in washing or cleaning agents in comparison with a reference mutation variant of the protease (SEQ ID NO:18 and/or SEQ ID NO:2 and/or SEQ ID NO: 19), in particular when stored for 3 or more days, 4 or more days, 7 or more days, 10 or more days, 12 or more days, 14 or more days, 21 or more days or 28 or more days. Such stability-enhanced proteases make it possible, even after a prolonged storage time, to achieve good washing results on proteolytically sensitive stains in various temperature ranges, in particular in a temperature range of from 20° C. to 40° C.

In addition to increased storage stability, the proteases may also have increased catalytic activity in washing or cleaning agents. In various embodiments, the proteases may have a proteolytic activity which, based on the wild type (SEQ ID NO:1), is at least 101%, such as at least 102% or more. In various embodiments, the proteases have a proteolytic activity which, based on a reference mutation variant of the protease (SEQ ID NO:1 and/SEQ ID NO:2 and/or SEQ ID NO: 19), is at least 110%, at least 115%, at least 120%, at least 125%, at least 130%, at least 135%, at least 140%, at least 145%, at least 150%, at least 155% or at least 160%. Such performance-enhanced proteases allow improved washing results on proteolytically sensitive stains in various temperature ranges, in particular in a temperature range of from 20° C. to 40° C.

The proteases exhibit enzymatic activity, i.e. they are capable of hydrolyzing peptides and proteins, in particular in a washing or cleaning agent. A protease is therefore an enzyme which catalyzes the hydrolysis of amide/peptide bonds in protein/peptide substrates and is thus able to cleave proteins or peptides. Furthermore, a protease is a mature protease, i.e. the catalytically active molecule without signal peptide(s) and/or propeptide(s). Unless stated otherwise, the sequences given also each refer to mature (processed) enzymes.

In various embodiments, the protease is a free enzyme. This means that the protease can act directly with all the components of an agent and, if the agent is a liquid agent, that the protease is in direct contact with the solvent of the agent (e.g. water). In other embodiments, an agent may contain proteases that form an interaction complex with other molecules or that contain a "coating." In this case, an individual protease molecule or multiple protease molecules may be separated from the other constituents of the agent by a surrounding structure. Such a separating structure may arise from, but is not limited to, vesicles such as a micelle or a liposome. The surrounding structure may also be a virus particle, a bacterial cell or a eukaryotic cell. In various embodiments, an agent may include cells of *Bacillus pumilus* or *Bacillus subtilis* which express the proteases, or cell culture supernatants of such cells.

In a further embodiment, the protease comprises an amino acid sequence which, over its entire length, is at least 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% and 98.8% identical to the amino acid sequence given in SEQ ID NO:1, and has the amino acid substitutions given above in each case based on the numbering according to SEQ ID NO:1. In the context of the present invention, the feature whereby a protease has the given substitutions means that it contains one (of the given) substitution(s) at the relevant position, i.e. at least the given positions are not otherwise mutated or deleted, for example by fragmenting of the protease. In various embodiments, it has amino acid substitutions (a) at the positions corresponding to positions 9 and 271, such that the amino acid substitutions are P9T, P9H, P9S or P9A and Q271E, and (b) has one or more of the amino acid substitutions 29G, 48V, 101E, 130D, 130S, 130H, 131S, 131N, 131D, 131K, 133K, 133R, 133Y, 144K, 144L, 144A, 224A, 224T or 252S at at least one of the positions corresponding to positions 29, 48, 101, 130, 131, 133, 144, 224 or 252 in the numbering according to SEQ ID NO:1. The amino acid sequences of such proteases which are suitable are given in SEQ ID Nos: 3-17 and 19-23. In various embodiments, the proteases described herein, with the exception of the explicitly mentioned substitutions, have the sequence of SEQ ID NO:1, i.e. apart from the substituted positions, they are 100% identical to the sequence according to SEQ ID NO:1.

The identity of nucleic acid or amino acid sequences is determined by a sequence comparison. This sequence comparison is based on the BLAST algorithm established and commonly used in the prior art (cf. for example Altschul et al. (1990): "Basic local alignment search tool," J. Mol. Biol. 215: 403-410, and Altschul et al. (1997): "Gapped BLAST and PSI-BLAST: a new generation of protein database search programs," Nucleic Acids Res. 25:3389-3402) and in principle occurs by associating similar sequences of nucleotides or amino acids in the nucleic acid or amino acid sequences. A tabular association of the positions concerned is referred to as alignment. Another algorithm available in the prior art is the FASTA algorithm. Sequence comparisons (alignments), in particular multiple sequence comparisons, are created using computer programs. The Clustal series (cf. for example, Chenna et al. (2003): "Multiple sequence alignment with the Clustal series of programs," Nucleic Acid Res. 31:3497-3500), T-Coffee (cf. for example, Notredame et al. (2000): "T-Coffee: A novel method for multiple sequence alignments," J. Mol. Biol. 302: 205-217) or programs based on these programs or algorithms are frequently used, for example. Sequence comparisons (alignments) using the computer program Vector NTI® Suite 10.3 (Invitrogen Corporation, 1600 Faraday Avenue, Carlsbad, Calif., USA) with the predetermined, default parameters, and the AlignX module of which for sequence comparisons is based on ClustalW, are also possible. Unless stated otherwise, the sequence identity given herein is determined by the BLAST algorithm.

Such a comparison also allows a statement regarding the similarity of the compared sequences. It is usually given in percent identity, i.e. the proportion of identical nucleotides or amino acid residues in said sequences or in an alignment of corresponding positions. The broader concept of homology takes conserved amino acid exchanges into account in the case of amino acid sequences, i.e. amino acids having similar chemical activity, since they usually perform similar chemical activities within the protein. Therefore, the similarity of the compared sequences may also be stated as percent homology or percent similarity. Identity and/or homology information can be provided regarding whole polypeptides or genes or only regarding individual regions. Homologous or identical regions of different nucleic acid or amino acid sequences are therefore defined by matches in the sequences. Such regions often have identical functions. They can be small and comprise only a few nucleotides or amino acids. Often, such small regions perform essential functions for the overall activity of the protein. It may therefore be expedient to relate sequence matches only to individual, optionally small regions. Unless stated otherwise, however, identity or homology information in the present application relates to the entire length of the particular nucleic acid or amino acid sequence indicated.

In the context, the indication that an amino acid position corresponds to a numerically designated position in SEQ ID NO:1 therefore means that the corresponding position is associated with the numerically designated position in SEQ ID NO:1 in an alignment as defined above.

In a further embodiment, the protease is characterized in that the cleaning performance thereof (after storage, e.g. over 4 weeks) is not significantly reduced compared with that of a protease comprising an amino acid sequence that corresponds to the amino acid sequence given in SEQ ID NO:18 and/or SEQ ID NO:2 and/or SEQ ID NO:19, i.e. has at least 80% of the reference washing performance, such as at least 100%, or at least 110% or more. The cleaning performance can be determined in a washing system containing a washing agent in a dosage between 4.5 and 7.0 grams per liter of washing liquor and the protease, the proteases to be compared being used in the same concentration (based on active protein) and the cleaning performance with respect to a stain on cotton being determined by measuring the degree of cleaning of the washed textiles. For example, the washing process can take place for 60 minutes at a temperature of 40° C. and the water can have a water hardness between 15.5 and 16.5° (German hardness). The concentration of the protease in the washing agent intended for this washing system is 0.001 to 0.1 wt. %, such as 0.01 to 0.06 wt. % based on active, purified protein.

A liquid reference washing agent for such a washing system may be composed as follows (all values in wt. %): 4.4% alkyl benzene sulfonic acid, 5.6% further anionic surfactants, 2.4% C12-C18 Na salts of fatty acids (soaps), 4.4% non-ionic surfactants, 0.2% phosphonates, 1.4% citric acid, 0.95% NaOH, 0.01% defoamer, 2% glycerol, 0.08% preservatives, 1% ethanol, and the remainder being demineralized water. In a non-limiting embodiment, the dosage of the liquid washing agent is between 4.5 and 6.0 grams per liter of washing liquor, for example 4.7, 4.9 or 5.9 grams per liter of washing liquor. Washing in a pH range between pH 7 and pH 10.5, such as between pH 7.5 and pH 8.5, is possible.

In the context, the cleaning performance is determined for example at 20° C. or 40° C. using a liquid washing agent as specified above, the washing process being carried out for 60 minutes at 600 rpm.

The degree of whiteness, i.e. the lightening of stains, as a measure of the cleaning performance is determined by optical measuring methods, such as photometrically. A suitable device for this purpose is for example the Minolta CM508d spectrometer. Usually, the devices used for the measurement are calibrated beforehand with a white standard, such as a supplied white standard.

The activity-equivalent use of the relevant protease ensures that the respective enzymatic properties, for example the cleaning performance on certain stains, are compared even if the ratio of active substance to total protein (the values of the specific activity) significantly differs. In general, a low specific activity can be compensated for by adding a larger amount of protein.

Otherwise, methods for determining protease activity are well known to, and routinely used by, a person skilled in the art of enzyme technology. For example, such methods are disclosed in Tenside, vol. 7 (1970), p. 125-132. Alternatively, the protease activity can be determined by the release of the chromophore para-nitroaniline (pNA) from the substrate suc-L-Ala-L-Ala-L-Pro-L-Phe-p-nitroanilide (AAPF). The protease cleaves the substrate and releases pNA. The release of the pNA causes an increase in absorbance at 410 nm, the temporal progression of which is a measure of the enzymatic activity (cf. Del Mar et al., 1979). The measurement is carried out at a temperature of 25° C., a pH of 8.6, and a wavelength of 410 nm. The measuring time is 5 min and the measuring interval is 20 s to 60 s. The protease activity is usually indicated in protease units (PE). Suitable protease activities amount for example to 2.25, 5 or 10 PE per ml of washing liquor. However, the protease activity is not equal to zero.

An alternative test for establishing the proteolytic activity of the proteases is an optical measuring method, such as a photometric method. The appropriate test comprises the protease-dependent cleavage of the substrate protein casein. This is cleaved by the protease into a multitude of smaller partial products. The totality of these partial products has an increased absorption at 290 nm compared with uncleaved casein, it being possible for this increased absorption to be determined using a photometer, and thus for a conclusion to be drawn regarding the enzymatic activity of the protease.

The protein concentration can be determined using known methods, for example the BCA method (bicinchoninic acid; 2,2'-bichinolyl-4,4'-dicarboxylic acid) or the Biuret method (A. G. Gornall, C. S. Bardawill and M. M. David, J. Biol. Chem., 177 (1948), p. 751-766). The active protein concentration can be determined in this regard by titrating the active centers using a suitable irreversible inhibitor and determining the residual activity (cf. M. Bender et al., J. Am. Chem. Soc. 88, 24 (1966), p. 5890-5913).

In addition to the amino acid alterations discussed above, proteases can have other amino acid alterations, in particular amino acid substitutions, insertions or deletions. Such proteases are, for example, further developed by targeted genetic modification, i.e. by mutagenesis methods, and optimized for specific applications or with regard to specific properties (for example with regard to their catalytic activity, stability, etc.). Furthermore, nucleic acids can be introduced into recombination approaches and can thus be used to generate completely novel proteases or other polypeptides.

The aim is to introduce targeted mutations such as substitutions, insertions or deletions into the known molecules in order, for example, to improve the cleaning performance of enzymes. For this purpose, in particular the surface charges and/or the isoelectric point of the molecules and thus their interactions with the substrate can be altered. For instance, the net charge of the enzymes can be altered in order to influence the substrate binding, in particular for use in washing and cleaning agents. Alternatively or in addition, one or more corresponding mutations can increase the stability or catalytic activity of the protease and thus improve its cleaning performance. Advantageous properties of individual mutations, e.g. individual substitutions, can complement one another. A protease which has already been optimized with regard to specific properties, for example with respect to its stability during storage, can therefore also be further developed.

For the description of substitutions relating to exactly one amino acid position (amino acid exchanges), the following convention is used herein: first, the naturally occurring amino acid is designated in the form of the internationally used one-letter code, followed by the associated sequence position and finally the inserted amino acid. Several exchanges within the same polypeptide chain are separated by slashes. For insertions, additional amino acids are named following the sequence position. In the case of deletions, the missing amino acid is replaced by a symbol, for example a star or a dash, or a 4 is indicated before the corresponding position. For example, P9T describes the substitution of proline at position 9 by threonine, P9TH describes the insertion of histidine following the amino acid threonine at position 9 and P9* or ΔP9 describes the deletion of proline at position 9. This nomenclature is known to a person skilled in the field of enzyme technology.

A protease may be characterized in that it is obtainable from a protease as described above as the starting molecule by one-time or multiple conservative amino acid substitution, the protease in the numbering according to SEQ ID NO:1 having the above-described amino acid substitutions. The term "conservative amino acid substitution" means the exchange (substitution) of one amino acid residue for another amino acid residue, with this exchange not resulting in a change to the polarity or charge at the position of the exchanged amino acid, e.g. the exchange of a nonpolar amino acid residue for another nonpolar amino acid residue. Conservative amino acid substitutions include, for example: G=A=S, I=V=L=M, D=E, N=Q, K=R, Y=F, S=T, G=A=I=V=L=M=Y=F=W=P=S=T.

Alternatively or in addition, the protease is characterized in that it is obtainable from a protease as a starting molecule by fragmentation or deletion, insertion or substitution mutagenesis and comprises an amino acid sequence which matches the starting molecule over a length of at least 200, 210, 220, 230, 240, 250, 260, 261, 262, 263, 264, 265, 266, 267, 268, 269, 270, 271, 272, 273, or 274 or 275 contiguous amino acids, the amino acid substitution(s) which is/are described above and possibly contained in the starting molecule, i.e. the substitutions at the positions corresponding to positions 9, 29, 48, 101, 130, 131, 133, 144, 216, 224, 252 and 271 in SEQ ID NO:1, and optionally the amino acid substitution 166M, 166Q or 166A at the position corresponding to position 166, and/or at least one further amino acid substitution at at least one of positions corresponding to positions 62, 133, 149, 156, 172 or 217, still being present.

For instance, it is possible to delete individual amino acids at the termini or in the loops of the enzyme without the proteolytic activity being lost or diminished in the process. Furthermore, such fragmentation or deletion, insertion or substitution mutagenesis can also, for example, reduce the allergenicity of the enzymes concerned and thus improve their overall applicability. Advantageously, the enzymes retain their proteolytic activity even after mutagenesis, i.e. their proteolytic activity corresponds at least to that of the starting enzyme, i.e. in a non-limiting embodiment the proteolytic activity is at least 80%, such as at least 90% of the activity of the starting enzyme. Other substitutions can also exhibit advantageous effects. Both single and multiple contiguous amino acids can be exchanged for other amino acids.

Alternatively or in addition, the protease is characterized in that it is obtainable from a protease as the starting molecule by one-time or multiple conservative amino acid substitution, the protease having (i) the amino acid substitutions P9T, P9H, P9S or P9A and Q271E at the positions corresponding to positions 9 and 271 according to SEQ ID NO:1, and (ii) at least one of the amino acid substitutions A29G, A48V, D101E, N130D, N130S, N130H, G131S, G131N, G131D, G131K, T133K, T133R, T133Y, N144K, N144L, N144A, S224A, S224T or N252S at the positions corresponding to positions 29, 48, 101, 130, 131, 133, 144, 224 and 252 according to SEQ ID NO:1, and optionally the amino acid substitution 166M, 166Q or 166A at the position corresponding to position 166, and/or at least one further amino acid substitution at at least one of the positions corresponding to positions 62, 133, 149, 156, 172 or 217.

In further embodiments, the protease is characterized in that it is obtainable from a protease as the starting molecule by fragmentation or deletion, insertion or substitution mutagenesis and comprises an amino acid sequence which matches the starting molecule over a length of at least 200, 210, 220, 230, 240, 250, 260, 261, 262, 263, 264, 265, 266, 267, 268, 269, 270, 271, 272, 273, or 274 or 275 contiguous amino acids, the protease comprising (i) the amino acid substitutions P9T, P9H, P9S or P9A and Q271E at the positions corresponding to positions 9 and 271 according to SEQ ID NO:1, and (ii) at least one of the amino acid substitutions A29G, A48V, D101E, N130D, N130S, N130H, G131S, G131N, G131D, G131K, T133K, T133R, T133Y, N144K, N144L, N144A, S224A, S224T or N252S at the positions corresponding to positions 29, 48, 101, 130, 131, 133, 144, 224 and 252 according to SEQ ID NO:1, and optionally the amino acid substitution 166M, 166Q or 166A at the position corresponding to position 166, and/or at least one further amino acid substitution at at least one of the positions corresponding to positions 62, 133, 149, 156, 172 or 217.

The further amino acid positions are in this case defined by an alignment of the amino acid sequence of a protease with the amino acid sequence of the protease from *Bacillus pumilus*, as given in SEQ ID NO:1. Furthermore, the assignment of the positions depends on the mature protein. This assignment is in particular also to be used if the amino acid sequence of a protease comprises a higher number of amino acid residues than the protease from *Bacillus pumilus* according to SEQ ID NO:1. Proceeding from the above-mentioned positions in the amino acid sequence of the protease from *Bacillus pumilus*, the alteration positions in a protease are those which are assigned to precisely these positions in an alignment.

Advantageous positions for sequence alterations, in particular substitutions, of the protease from *Bacillus pumilus*, which are of particular significance when transferred to homologous positions of the proteases and which impart advantageous functional properties to the protease are therefore the positions which correspond to positions 9, 29, 48, 62, 101, 130, 131, 133, 144, 149, 156, 166, 172, 216, 217, 224, 252 and 271 in SEQ ID NO:1 in an alignment, i.e. in the numbering according to SEQ ID NO:1. At the positions mentioned, the following amino acid residues are present in the wild-type molecule of the protease from *Bacillus pumilus*: P9, A29, A48, Q62, D101, N130, G131, T133, N144, V149, S156, G166, D172, S216, Y217, S224, N252 and Q271.

Further confirmation of the correct assignment of the amino acids to be altered, i.e. in particular their functional correspondence, can be provided by comparative experiments, according to which the two positions assigned to one another on the basis of an alignment are altered in the same way in both compared proteases, and observations are made as to whether the enzymatic activity is altered in the same way in both cases. If, for example, an amino acid exchange in a specific position of the protease from *Bacillus pumilus* according to SEQ ID NO:1 is accompanied by an alteration of an enzymatic parameter, for example an increase in the $K_M$ value, and a corresponding alteration of the enzymatic parameter, for example likewise an increase in the $K_M$ value, is observed in a protease variant of which the amino acid exchange has been achieved by the same introduced amino acid, this can therefore be considered to be confirmation of the correct assignment.

All of these aspects are also applicable to the method for producing a protease. Accordingly, a method further comprises one or more of the following method steps:
  a) Introducing one-time or multiple conservative amino acid substitution, the protease comprising
     (i) the amino acid substitutions P9T, P9H, P9S or P9A and Q271E at the positions corresponding to positions 9 and 271 according to SEQ ID NO:1, and
     (ii) at least one of the amino acid substitutions A29G, A48V, D101E, N130D, N130S, N130H, G131S, G131N, G131D, G131K, T133K, T133R, T133Y, N144K, N144L, N144A, S224A, S224T or N252S at the positions corresponding to positions 29, 48, 101, 130, 131, 133, 144, 224 and 252 according to SEQ ID NO:1;
  b) Altering the amino acid sequence by fragmentation or deletion, insertion or substitution mutagenesis such that the protease comprises an amino acid sequence which matches the starting molecule over a length of at least 200, 210, 220, 230, 240, 250, 260, 261, 262, 263, 264, 265, 266, 267, 268, 269, 270, 271, 272, 273, or 274 or 275 contiguous amino acids, the protease comprising (i) the amino acid substitutions P9T, P9H, P9S or P9A and Q271E at the positions corresponding to positions 9 and 271 according to SEQ ID NO:1, and (ii) at least one of the amino acid substitutions A29G, A48V, D101E, N130D, N130S, N130H, G131S, G131N, G131D, G131K, T133K, T133R, T133Y, N144K, N144L, N144A, S224A, S224T or N252S at the positions corresponding to positions 29, 48, 101, 130, 131, 133, 144, 224 and 252 according to SEQ ID NO:1.

In various embodiments of this method, this comprises one or more of the following steps:

a) Introducing one-time or multiple conservative amino acid substitution into the protease, the protease comprising the substitutions 9T, 130D, 144K, 252T and 271E at the positions corresponding to positions 9, 130, 144, 252 and 271; and optionally the amino acid substitution 166M, 166Q or 166A at the position corresponding to position 166, and/or at least one further amino acid substitution at at least one of the positions corresponding to positions 62, 133, 149, 156, 172 or 217;

b) Altering the amino acid sequence by fragmentation or deletion, insertion or substitution mutagenesis such that the protease comprises an amino acid sequence which matches the starting molecule over a length of at least 200, 210, 220, 230, 240, 250, 260, 261, 262, 263, 264, 265, 266, 267, 268, 269, 270, 271, 272, 273 or 274 contiguous amino acids, the protease comprising the substitutions 9T, 130D, 144K, 252T and 271E at the positions corresponding to positions 9, 130, 144, 252 and 271; and optionally the amino acid substitution 166M, 166Q or 166A at the position corresponding to position 166, and/or at least one further amino acid substitution at at least one of the positions corresponding to positions 62, 133, 149, 156, 172 or 217.

All embodiments also apply to the method.

In further embodiments, the protease or the protease produced by means of a method is still at least 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, or 98.8% identical to the amino acid sequence given in SEQ ID NO:1 over its entire length. Alternatively, the protease or the protease produced by means of a method is still at least 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, or 98% identical to one of the amino acid sequences given in SEQ ID Nos: 3-17 or 19-23 over its entire length. The protease or the protease produced by means of a method has an amino acid substitution at positions 9 and 271 and at least one of the positions corresponding to positions 29, 48, 101, 130, 131, 133, 144, 224 or 252, in each case based on the numbering according to SEQ ID NO:1. In more embodiments, the amino acid substitution is at least one selected from the group consisting of P9T, P9H, P9S, P9A, A29G, A48V, D101E, N130D, N130S, N130H, G131S, G131N, G131D, G131K, T133K, T133R, T133Y, N144K, N144L, N144A, S224A, S224T, N252S and Q271E, in each case based on the numbering according to SEQ ID NO:1. In further embodiments, the protease further comprises a substitution at the position 216, in particular S216C; in various embodiments it may be optional for this position to not be substituted. The following amino acid substitution variants are most particularly suitable: P9T, P9H, P9S or P9A, in particular P9T, and Q271E and optionally also S216C combined with one of (i) N130D, G131S, T133Y and S224A; (ii) N130S, G131S, T133Y, N144L and S224A; (iii) N130D, G131N, T133K and N144K; (iv) N130H, G131N, N144K and S224A; (v) A29G, N130D, G131N and T133R; (vi) A29G, D101E, N130S, G131S, S224T and N252S; (vii) N130H, G131S and S224A; (viii) N130D, G131S, T133K and S224A; (ix) A29G, D101E, N130D, G131K and S224A; (x) N130D, G131N T133K, N144L and N252S; (xi) G131S, N144K and S224T; (xii) D101E, N130D, G131S, T133Y, N144A and S224A; (xiii) A29G, D101E, N130S, S224T and N252S; (xiv) A48V, G131S, T133R and S224A; or (xv) G131D, T133R and S224A, the numbering being based in each case on the numbering according to SEQ ID NO:1.

In further embodiments, the protease or the protease produced by means of a method has the amino acid substitutions 9T, 130D, 144K, 252T and 271E at the positions corresponding to positions 9, 130, 144, 252 and 271; and optionally the amino acid substitution 166M, 166Q or 166A at the position corresponding to position 166, and/or at least one further amino acid substitution at at least one of the positions corresponding to positions 62, 133, 149, 156, 172 or 217, in each case based on the numbering according to SEQ ID NO:1. Examples thereof are the following amino acid substitution variants: P9T and Q271E combined with one of (i) N130D, N144K, N252T and G166M; (ii) N130D, N144K, N252T and G166Q; (iii) N130D, N144K, N252T and G166A; (iv) N130D, N144K, N252T and S156G; or (v) N130D, N144K, N252T and Y217M, the numbering being based in each case on the numbering according to SEQ ID NO:1 and the variants described in the examples.

A protease described above that may be additionally stabilized, in particular by one or more mutations, for example substitutions, or by coupling to a polymer. An increase in stability during storage and/or during use, for example in the washing process, leads to longer enzymatic activity and thus improves the cleaning performance. In principle, all stabilization options which are described in the prior art and/or are appropriate are considered. Those stabilizations are suitable which are achieved by mutations of the enzyme itself, since such stabilizations do not require any further work steps following the recovery of the enzyme. Examples of sequence alterations suitable for this purpose are mentioned above. Further suitable sequence alterations are known from the prior art.

Further possibilities for stabilization are, for example:

Altering the binding of metal ions, in particular the calcium binding sites, for example by exchanging one or more of the amino acids involved in the calcium binding with one or more negatively charged amino acids and/or by introducing sequence alterations into at least one of the results of the two amino acids arginine/glycine;

Protecting against the influence of denaturing agents such as surfactants by mutations that cause an alteration of the amino acid sequence on or at the surface of the protein;

Replacing amino acids which are close to the N-terminus with those likely to contact the rest of the molecule via non-covalent interactions, thus contributing to the maintenance of the globular structure.

Non-limiting embodiments are those in which the enzyme is stabilized in several ways, since several stabilizing mutations have an additive or synergistic effect.

A protease as described above that may be characterized in that it has at least one chemical modification. A protease having such an alteration is called a derivative, i.e. the protease is derivatized.

In the context of the present application, derivatives are thus understood to mean those proteins of which the pure amino acid chain has been chemically modified. Such derivatizations can be achieved, for example, in vivo by the host cell that expresses the protein. In this regard, couplings of low-molecular-weight compounds such as lipids or oligosaccharides are particularly noteworthy. However, the derivatizations may also be carried out in vitro, for example by the chemical conversion of a side chain of an amino acid or by covalent bonding of another compound to the protein. For example, it is possible to couple amines to carboxyl groups of an enzyme in order to alter the isoelectric point. Another such compound may also be another protein that is bound to a protein via bifunctional chemical compounds, for example. Derivatization is also understood to mean the covalent bonding to a macromolecular carrier or a non-covalent inclusion in suitable macromolecular cage structures. Derivatizations may, for example, affect the substrate specificity or bonding strength to the substrate or cause a temporary blockage of the enzymatic activity when the coupled substance is an inhibitor. This can be expedient, for example, for the period of the storage. Such modifications may further affect the stability or enzymatic activity. They can also be used to reduce the allergenicity and/or immunogenicity of the protein and thus, for example, increase its skin compatibility. For example, couplings with macromolecular compounds, for example polyethylene glycol, can improve the protein in terms of stability and/or skin compatibility.

Derivatives of a protein can also be understood in the broadest sense to mean preparations of these proteins. Depending on the recovery, processing or preparation, a protein can be combined with various other substances, for example from the culture of the producing microorganisms. A protein may also have been deliberately added to other substances, for example to increase its storage stability. This is also irrespective of whether or not it actually exhibits this enzymatic activity in a particular preparation. This is because it may be desired that it has no or only low activity during storage, and exhibits its enzymatic function only at the time of use. This can be controlled via appropriate accompanying substances, for example. In particular, the joint preparation of proteases with specific inhibitors is possible in this regard.

Of all the proteases or protease variants and/or derivatives described above, those of which the storage stability corresponds to at least one of those of the proteases according to SEQ ID Nos: 3-17 or 19-23, and/or of which the cleaning performance corresponds to at least one of those of the proteases according to SEQ ID Nos: 3-17 or 19-23, are particularly possible, the cleaning performance being determined in a washing system as described above.

A nucleic acid which codes for a protease, as well as to a vector containing such a nucleic acid, in particular a cloning vector or an expression vector.

These may be DNA or RNA molecules. They can be present as a single strand, as a single strand that is complementary to this single strand, or as a double strand. In particular in the case of DNA molecules, the sequences of the two complementary strands must be taken into account in all three possible reading frames. Furthermore, it should be noted that different codons, i.e. base triplets, can code for the same amino acids such that a particular amino acid sequence can be coded by a plurality of different nucleic acids. Due to this degeneracy of the genetic code, all of the nucleic acid sequences which can code any of the proteases described above are included. A person skilled in the art is able to determine these nucleic acid sequences unequivocally since, despite the degeneracy of the genetic code, defined amino acids can be assigned to individual codons. Therefore, a person skilled in the art proceeding from an amino acid sequence can easily determine nucleic acids coding for said amino acid sequence. Furthermore, in the case of nucleic acids, one or more codons may be replaced by synonymous codons. This aspect relates in particular to the heterologous expression of the enzymes. For instance, every organism, for example a host cell of a production strain, has a particular codon usage. Codon usage is understood to mean the translation of the genetic code into amino acids by the particular organism. Bottlenecks can occur in the protein biosynthesis if the codons on the nucleic acid in the organism are faced with a comparatively small number of loaded tRNA molecules. Although coding for the same amino acid, this results in a codon being translated less efficiently in the organism than a synonymous codon coding for the same amino acid. Due to the presence of a higher number of tRNA molecules for the synonymous codon, it can be translated more efficiently in the organism.

Using methods which are currently generally known, such as chemical synthesis or the polymerase chain reaction (PCR), in conjunction with molecular-biological and/or protein-chemical standard methods, it is possible for a person skilled in the art to produce the corresponding nucleic acids and even complete genes on the basis of known DNA and/or amino acid sequences. Such methods are known for example from Sambrook, J., Fritsch, E. F. and Maniatis, T. 2001. Molecular cloning: a laboratory manual, 3. Edition Cold Spring Laboratory Press.

Within the meaning herein, vectors are understood to mean elements consisting of nucleic acids, which elements contain a nucleic acid as the characteristic nucleic acid region. They are able to establish these as a stable genetic element in a species or cell line over several generations or cell divisions. Vectors are special plasmids, i.e. circular genetic elements, in particular when used in bacteria. A nucleic acid is cloned into a vector. The vectors include, for example, those originating from bacterial plasmids, viruses or bacteriophages, or predominantly synthetic vectors or plasmids with elements of a wide variety of origins. With the additional genetic elements present in each case, vectors are able to establish themselves as stable units in the corresponding host cells over several generations. They may be present as separate units in an extrachromosomal manner or integrated into a chromosome or chromosomal DNA.

Expression vectors comprise nucleic acid sequences which enable them to replicate in the host cells containing them, such as microorganisms, e.g. bacteria, and to express a contained nucleic acid there. The expression is in particular influenced by the promoter(s) that regulate the transcription. In principle, the expression can take place by the natural promoter originally located before the nucleic acid to be expressed, but also by a promoter of the host cell provided on the expression vector or also by a modified or completely different promoter of another organism or another host cell. In the present case, at least one promoter is provided for the expression of a nucleic acid and used for the expression thereof. Furthermore, expression vectors can be regulatable, for example by changing the cultivation conditions or when a specific cell density of the host cells containing them is reached or by addition of specific substances, in particular activators of gene expression. An example of such a substance is the galactose derivative isopropyl-β-D-thiogalactopyranoside (IPTG), which is used as an activator of the bacterial lactose operon (lac operon). In contrast with expression vectors, the nucleic acid contained is not expressed in cloning vectors.

A non-human host cell which contains a nucleic acid or a vector or which contains a protease, in particular one which secretes the protease into the medium surrounding the host cell. In a non-limiting embodiment, a nucleic acid or a vector is transformed into a microorganism, which then represents a host cell. Alternatively, individual components, i.e. nucleic acid parts or fragments of a nucleic acid can be introduced into a host cell such that the resulting host cell contains a nucleic acid or a vector. This procedure is particularly suitable when the host cell already contains one or more constituents of a nucleic acid or a vector and the further constituents are then supplemented accordingly. Methods for transforming cells are established in the prior art and are well known to a person skilled in the art. In principle, all cells, i.e. prokaryotic or eukaryotic cells, are suitable as host cells. Host cells that can be managed in a genetically advantageous manner, for example in terms of the transformation with the nucleic acid or the vector and the stable establishment thereof, are possible, for example unicellular fungi or bacteria. Furthermore, host cells are characterized by good microbiological and biotechnological manageability. This relates, for example, to easy cultivation, high growth rates, low requirements for fermentation media and good production and secretion rates for foreign proteins. Non-limiting host cells secrete the (transgenically) expressed protein into the medium surrounding the host cells. Furthermore, the proteases can be modified by the cells producing them after their production, for example by attachment of sugar molecules, formylations, aminations, etc. Such post-translational modifications can functionally influence the protease.

Other embodiments are those host cells of which the activity can be regulated on account of genetic regulatory elements, which are, for example, made available on the vector but may also be present in these cells from the outset. These host cells may be induced to express for example by the controlled addition of chemical compounds which are used as activators, by changing the cultivation conditions, or upon reaching a specific cell density. This enables an economical production of the proteins. An example of such a compound is IPTG as described above.

Prokaryotic or bacterial cells are suitable host cells. Bacteria are characterized by short generation times and low demands on cultivation conditions. As a result, cost-effective cultivation methods or production methods can be established. In addition, a person skilled in the art has a wealth of experience in the case of bacteria in fermentation technology. For a specific production, gram-negative or gram-positive bacteria may be suitable for a wide variety of reasons to be determined experimentally in individual cases, such as nutrient sources, product formation rate, time requirement, etc.

In the case of gram-negative bacteria, such as *Escherichia coli*, a large number of proteins are secreted into the periplasmic space, i.e. into the compartment between the two membranes enclosing the cells. This may be advantageous for particular applications. Furthermore, gram-negative bacteria can also be designed such that they eject the expressed proteins not only into the periplasmic space, but into the medium surrounding the bacterium. In contrast, gram-positive bacteria such as bacilli or actinomycetes or other representatives of *Actinomycetales* have no outer membrane, and therefore secreted proteins are released immediately into the medium surrounding the bacteria, usually the nutrient medium, from which the expressed proteins can be purified. They can be isolated directly from the medium or further processed. In addition, gram-positive bacteria are related or identical to most of the origin organisms for technically significant enzymes and usually even form comparable enzymes, meaning that they have a similar codon usage and the protein synthesis apparatus is naturally aligned accordingly.

Host cells may be altered in terms of their requirements for the culture conditions, may have different or additional selection markers or may express other or additional proteins. In particular, this may also involve those host cells which transgenically express several proteins or enzymes.

Microorganisms, in particular fermentable microorganisms, such as those of the genus *Bacillus*, and leads to it being possible to produce proteins by the use of such microorganisms. Such microorganisms then represent host cells.

In a further embodiment, the host cell is characterized in that it is a bacterium, such as one selected from the group of the genera of *Escherichia*, *Klebsiella*, *Bacillus*, *Staphylococcus*, *Corynebacterium*, *Arthrobacter*, *Streptomyces*, *Stenotrophomonas* and *Pseudomonas*, more suitably one selected from the group of *Escherichia coli*, *Klebsiella planticola*, *Bacillus licheniformis*, *Bacillus lentus*, *Bacillus amyloliquefaciens*, *Bacillus subtilis*, *Bacillus alcalophilus*, *Bacillus globigii*, *Bacillus gibsonii*, *Bacillus clausii*, *Bacillus halodurans*, *Bacillus pumilus*, *Staphylococcus carnosus*, *Corynebacterium glutamicum*, *Arthrobacter oxidans*, *Streptomyces lividans*, *Streptomyces coelicolor* and *Stenotrophomonas maltophilia*.

The host cell may also be a eukaryotic cell, however, which is characterized in that it has a cell nucleus. A host cell may be characterized in that it has a cell nucleus. In contrast with prokaryotic cells, eukaryotic cells are capable of post-translationally modifying the protein formed. Examples thereof are fungi such as actinomycetes or yeasts such as *Saccharomyces* or *Kluyveromyces*. This can be particularly advantageous, for example, if the proteins are to undergo specific modifications in connection with their synthesis that make such systems possible. Modifications carried out by eukaryotic systems, in particular in connection with the protein synthesis, include, for example, the binding of low-molecular-weight compounds such as membrane anchors or oligosaccharides. Such oligosaccharide modifications may be desirable, for example, to lower the allergenicity of an expressed protein. Co-expression with the enzymes naturally formed by such cells, such as cellulases, may be advantageous. Furthermore, for example, thermophilic fungal expression systems may be particularly suitable for the expression of temperature-resistant proteins or variants.

The host cells are cultivated and fermented in the conventional way, for example in discontinuous or continuous systems. In the first case, a suitable nutrient medium is inoculated with the host cells and the product is harvested from the medium after a period to be determined experimentally. Continuous fermentations are characterized by the achievement of a flow equilibrium, in which cells partially die over a comparatively long period of time but also grow back and the protein formed can be removed from the medium at the same time.

Host cells are used to produce proteases. A method for preparing a protease, may include
a) cultivating a host cell, and
b) isolating the protease from the culture medium or from the host cell.

This subject matter comprises fermentation processes. Fermentation processes are known per se from the prior art and represent the actual large-scale production step, usually followed by a suitable purification method of the produced product, for example the proteases. All fermentation processes which are based on a corresponding method for producing a protease constitute embodiments of this subject matter.

Fermentation processes which are characterized in that the fermentation is carried out via a feed strategy shall be considered in particular. In this case, the media components that are consumed by the continuous cultivation are added. As a result, considerable increases can be achieved both in the cell density and in the cell mass or dry mass and/or in particular in the activity of the protease of interest. Furthermore, the fermentation can also be designed in such a way that undesired metabolic products are filtered out or neutralized by adding buffers or suitable counter ions.

The protease produced can be harvested from the fermentation medium. Such a fermentation process is better than isolation of the protease from the host cell, i.e. product preparation from the cell mass (dry matter), but requires the provision of suitable host cells or one or more suitable secretion markers or mechanisms and/or transport systems for the host cells to secrete the protease into the fermentation medium. Without secretion, the protease can alternatively be isolated from the host cell, i.e. purified from the cell mass, for example by precipitation with ammonium sulphate or ethanol, or by chromatographic purification.

All of the above-mentioned aspects can be combined into methods in order to produce protease.

An agent may be characterized in that it contains a protease as described above. The agent is a washing or cleaning agent.

This subject matter covers all conceivable types of washing or cleaning agents, both concentrates and agents to be used undiluted, for use on a commercial scale, in washing machines or for hand washing or cleaning. These include, for example, washing agents for textiles, carpets, or natural fibers, for which the term washing agent is used. These also include, for example, dishwashing detergents for dishwashers or manual dishwashing detergents or cleaners for hard surfaces such as metal, glass, porcelain, ceramics, tiles, stone, painted surfaces, plastics, wood or leather, for which the term cleaning agent is used, i.e. in addition to manual and mechanical dishwashing detergents, also, for example, scouring agents, glass cleaners, toilet rim blocks, etc. The washing and cleaning agents also include auxiliary washing agents which are added to the actual washing agent during manual or automatic textile washing in order to achieve a further effect. Furthermore, washing and cleaning agents also include textile pre-treatment and post-treatment agents, i.e. those agents with which the item of laundry is brought into contact before the actual washing cycle, for example to loosen stubborn soiling, and also those agents which give the laundry further desirable properties such as a pleasant feel, crease resistance or low static charge in a step subsequent to the actual textile wash. Inter alia, softeners are included in the last-mentioned agents.

The washing or cleaning agents, which may be in the form of powdered solids, in further-compacted particulate form, homogeneous solutions or suspensions, may contain, in addition to a protease, all known ingredients conventional in such agents, with at least one other ingredient being present in the agent. The agents may in particular contain surfactants, builders, peroxygen compounds or bleach activators. They may also contain water-miscible organic solvents, further enzymes, sequestering agents, electrolytes, pH regulators and/or further auxiliaries such as optical brighteners, graying inhibitors, foam regulators, as well as dyes and fragrances, and combinations thereof.

In particular, a combination of a protease with one or more further ingredients of the agent is advantageous, since, in embodiments, such an agent has improved cleaning performance by virtue of resulting synergisms. In particular, combining a protease with a surfactant and/or a builder and/or a peroxygen compound and/or a bleach activator can result in such a synergism. However, in embodiments, the agent may not contain boric acid.

Advantageous ingredients of agents are disclosed in international patent application WO2009/121725, starting at the penultimate paragraph of page 5 and ending after the second paragraph on page 13. Reference is expressly made to this disclosure and the disclosure therein is incorporated in the present patent application by reference.

An agent advantageously contains the protease in an amount of from 2 µg to 20 mg, such as from 5 µg to 17.5 mg, alternatively from 20 µg to 15 mg or from 50 µg to 10 mg per g of the agent. In various embodiments, the concentration of the protease (active enzyme) described herein in the agent is >0 to 1 wt. %, such as 0.001 to 0.1 wt. %, based on the total weight of the agent or composition. Further, the protease contained in the agent, and/or other ingredients of the agent, may be coated with a substance which is impermeable to the enzyme at room temperature or in the absence of water, and which becomes permeable to the enzyme under conditions of use of the agent. Such an embodiment is thus characterized in that the protease is coated with a substance which is impermeable to the protease at room temperature or in the absence of water. Furthermore, the washing or cleaning agent itself can be packed in a container, such as an air-permeable container, from which it is released shortly before use or during the washing process.

In further embodiments, the agent is characterized in that it
  (a) is present in solid form, in particular as a flowable powder having a bulk density of from 300 g/l to 1200 g/l, in particular from 500 g/l to 900 g/l, or
  (b) is present in paste or liquid form, and/or
  (c) is present in the form of a gel or in the form of dosing pouches, and/or
  (d) is present as a single-component system, or
  (e) is divided into a plurality of components.

These embodiments include all solid, powdered, liquid, gel or paste administration forms of agents, which may optionally also consist of a plurality of phases and can be present in compressed or uncompressed form. The agent may be present as a flowable powder, in particular having a bulk density of from 300 g/l to 1200 g/l, in particular from 500 g/l to 900 g/l or from 600 g/l to 850 g/l. The solid administration forms of the agent also include extrudates, granules, tablets or pouches. Alternatively, the agent may also be in liquid, gel or paste form, for example in the form of a non-aqueous liquid washing agent or a non-aqueous paste or in the form of an aqueous liquid washing agent or a water-containing paste. The agent may also be present as a one-component system. Such agents consist of one phase.

Alternatively, an agent may also consist of a plurality of phases. Such an agent is therefore divided into a plurality of components.

Washing or cleaning agents may contain only one protease.

Alternatively, they may also contain other hydrolytic enzymes or other enzymes in a concentration that is expedient for the effectiveness of the agent. A further embodiment is therefore represented by agents which further comprise one or more further enzymes. Further enzymes which can be used are all enzymes which can exhibit catalytic activity in the agent, in particular a lipase, amylase, cellulase, hemicellulase, mannanase, tannase, xylanase, xanthanase, xytoglucanase, β-glucosidase, pectinase, carrageenase, perhydrolase, oxidase, oxidoreductase or another protease, which is different from the proteases, as well as mixtures thereof. Further enzymes are advantageously contained in the agent in an amount of from $1 \times 10^{-8}$ to 5 wt. % based on active protein. Each further enzyme may be contained in agents in an amount of from $1 \times 10^{-7}$ to 3 wt. %, from 0.00001 to 1 wt. %, from 0.00005 to 0.5 wt. %, from 0.0001 to 0.1 wt. % and such as from 0.0001 to 0.05 wt. %, based on active protein. In a non-limiting embodiment, the enzymes exhibit synergistic cleaning performance against specific stains or spots, i.e. the enzymes contained in the agent composition support one another in their cleaning performance. There is such synergism between the protease and a further enzyme of an agent, including in particular between said protease and an amylase and/or a lipase and/or a mannanase and/or a cellulase and/or a pectinase. Synergistic effects can arise not only between different enzymes, but also between one or more enzymes and other ingredients of the agent.

In the cleaning agents described herein, the enzymes to be used may furthermore be formulated together with accompanying substances, for example from fermentation. In liquid formulations, the enzymes are used as enzyme liquid formulations.

The enzymes are generally not provided in the form of pure protein, but rather in the form of stabilized, storable and transportable preparations. These pre-formulated preparations include, for example, the solid preparations obtained through granulation, extrusion, or lyophilization or, in particular in the case of liquid or gel agents, solutions of the enzymes, advantageously maximally concentrated, low-water, and/or supplemented with stabilizers or other auxiliaries.

Alternatively, the enzymes can also be encapsulated, for both the solid and the liquid administration form, for example by spray-drying or extrusion of the enzyme solution together with a natural polymer or in the form of capsules, for example those in which the enzymes are enclosed in a set gel, or in those of the core-shell type, in which an enzyme-containing core is coated with a water-, air-, and/or chemical-impermeable protective layer. Other active ingredients such as stabilizers, emulsifiers, pigments, bleaching agents, or dyes can additionally be applied in overlaid layers. Such capsules are applied using inherently known methods, for example by shaking or roll granulation or in fluidized bed processes. Such granules are advantageously low in dust, for example due to the application of polymeric film-formers, and are stable in storage due to the coating.

Moreover, it is possible to formulate two or more enzymes together, such that a single granule exhibits a plurality of enzyme activities.

The enzymes can also be incorporated in water-soluble films, such as those used in the formulation of washing and cleaning agents in a unit dosage form. Such a film allows the release of the enzymes following contact with water. As used herein, "water-soluble" refers to a film structure that is completely water-soluble. In a non-limiting embodiment, such a film consists of (fully or partially hydrolyzed) polyvinyl alcohol (PVA).

A method for cleaning textiles or hard surfaces may be characterized in that an agent is used in at least one method step, or in that a protease becomes catalytically active in at least one method step, in particular such that the protease is used in an amount of from 40 μg to 4 g, such as from 50 μg to 3 g, alternatively from 100 μg to 2 g, or from 200 μg to 1 g.

In various embodiments, the method described above is characterized in that the protease is used at a temperature of from 0 to 100° C., such as 0 to 60° C., alternatively 20 to 40° C. or at 20 or 25° C.

These include both manual and mechanical methods. Methods for cleaning textiles are generally characterized by the fact that, in a plurality of method steps, various cleaning-active substances are applied to the material to be cleaned and washed off after the exposure time, or in that the material to be cleaned is otherwise treated with a washing agent or a solution or dilution of this agent. The same applies to methods for cleaning all materials other than textiles, in particular hard surfaces. All conceivable washing or cleaning methods can be enhanced in at least one of the method steps by the use of a washing or cleaning agent or a protease, and then represent embodiments. All aspects, objects, and embodiments described for the protease and agents containing it are also applicable to this subject matter. Therefore, reference is expressly made at this point to the disclosure at the appropriate point with the note that this disclosure also applies to the above-described method.

Since proteases naturally already have hydrolytic activity and also exhibit this in media which otherwise have no cleaning power, for example in a simple buffer, a single and/or the sole step of such a method can consist in the protease, which is the only cleaning-active component, being brought into contact with the stain, in a buffer solution or in water. This represents a further embodiment of this subject matter.

Alternative embodiments are also represented by methods for treating textile raw materials or for textile care, in which a protease becomes active in at least one method step. Among these, methods for textile raw materials, fibers or textiles with natural components are suitable, and especially for those with wool or silk.

Finally, the proteases described herein may be used in washing or cleaning agents, for example as described above, for the (improved) removal of protein-containing stains, for example from textiles or hard surfaces. In embodiments of this use, the protease in the washing or cleaning agent is stored for 3 or more days, 4 or more days, 7 or more days, 10 or more days, 12 or more days, 14 or more days, 21 or more days or 28 or more days before a washing or cleaning process.

All aspects, objects, and embodiments described for the protease and agents containing it are also applicable to this subject matter. Therefore, reference is expressly made at this point to the disclosure at the appropriate point with the note that this disclosure also applies to the above-described use.

Examples

Overview of the Mutations:

A subtilisin-type alkaline protease from *Bacillus pumilus* may be useable herein. From this protease (SEQ ID NO:1), variants were produced by random mutagenesis, which were then screened, inter alia for improved washing performance and/or enzyme stability. In this way, two performance-enhanced mutants (mutant 1 [SEQ ID NO:18] and mutant 2 [SEQ ID NO:2]) were generated from the wild-type protease mentioned above in a first round by error-prone mutagenesis. Both of these mutants were subject to an independent, second error-prone round. In this second round of mutation, mutants 3-17 according to SEQ ID Nos. 3-17 were generated. Therefore, all of mutants 3-17 mentioned here also carry at least some of the mutations of mutants 1 or 2. In a third round, another performance-enhanced mutant (mutant 18 [SEQ ID NO:19]) was generated by error-prone mutagenesis. This mutant was subject to a fourth error-prone round. In this fourth round of mutation, mutants 19-23 according to SEQ ID Nos. 20-24 were generated. Therefore, all of mutants 19-23 mentioned here also carry the mutations of mutant 18.

| Chemical name | Wt. % of active substance in the raw | Wt. % of active substance in the |
|---|---|---|
| Glycerol | 100 | 2 |
| Preservative | 100 | 0.08 |
| Ethanol | 93 | 1 |

Without opt. brighteners, perfume, dye and enzymes.
Dosage 4.7 g/L

Storage Stability Test 2:

| Chemical name | Wt. % of active substance in the raw | Wt. % of active substance in the |
|---|---|---|
| Demineralized water | 100 | Remainder |
| Alkyl benzene sulfonic acid | 96 | 12-18 |
| Anionic surfactants | 70 | 4-8 |
| C12-C18 fatty acid Na salt | 30 | 2-4 |

| Variant | Amino acid substitutions relative to SEQ ID NO: 1 | | | | | | | SEQ ID NO. |
|---|---|---|---|---|---|---|---|---|
| Mutant 1 | P9T | Q271E | S216C | | | | | 18 |
| Mutant 2 | P9T | Q271E | S216C | T133R | S224A | | | 2 |
| Mutant 3 | P9T | Q271E | S216C | N130D | G131S | T133Y | S224A | 3 |
| Mutant 4 | P9T | Q271E | S216C | N130S | G131S | T133Y | N144L | S224A | 4 |
| Mutant 5 | P9T | Q271E | S216C | N130D | G131N | T133K | N144k | 5 |
| Mutant 6 | P9T | Q271E | S216C | N130H | G131N | N144K | S224A | 6 |
| Mutant 7 | P9T | Q271E | S216C | A29G | N130D | G131N | T133R | 7 |
| Mutant 8 | P9T | Q271E | S216C | A29G | D101E | N130S | G131S | S224T | N252S | 8 |
| Mutant 9 | P9T | Q271E | S216C | N130H | G131S | S224A | | 9 |
| Mutant | P9T | Q271E | S216C | N130D | G131S | T133K | S224A | 10 |
| Mutant | P9T | Q271E | S216C | A29G | D101E | N130D | G131K | S224A | 11 |
| Mutant | P9T | Q271E | S216C | N130D | G131N | T133K | N144L | N252S | 12 |
| Mutant | P9T | Q271E | S216C | G131S | N144K | S224T | | 13 |
| Mutant | P9T | Q271E | S216C | D101E | N130D | G131S | T133Y | N144A | S224A | 14 |
| Mutant | P9T | Q271E | S216C | A29G | D101E | N130S | S224T | N252S | 15 |
| Mutant | P9T | Q271E | S216C | A48V | G131S | T133R | S224A | 16 |
| Mutant | P9T | Q271E | S216C | G131D | T133R | S224A | | 17 |
| Mutant | P9T | Q271E | | N130D | N144K | N252T | | 19 |
| Mutant | P9T | Q271E | | N130D | N144K | N252T | G166M | 20 |
| Mutant | P9T | Q271E | | N130D | N144K | N252T | G166Q | 21 |
| Mutant | P9T | Q271E | | N130D | N144K | N252T | G166A | 22 |
| Mutant | P9T | Q271E | | N130D | N144K | N252T | Y217M | 23 |
| Mutant | P9T | Q271E | | N130D | N144K | N252T | S156G | 24 |
| Mutant | P9T | Q271E | | N130D | N144K | N252T | D172P | |
| Mutant | P9T | Q271E | | N130D | N144K | N252T | V149I | |
| Mutant | P9T | Q271E | | N130D | N144K | N252T | Q62S | |
| Mutant | P9T | Q271E | | N130D | N144K | N252T | Y217M | T133R | |
| Mutant | P9T | Q271E | | | N144K | N252T | Y217M | |
| Mutant | P9T | Q271E | | N130D | N144K | N252T | S156Q | |

Washing Agent Matrix Used

The following washing agent matrices (commercially available, without enzymes, opt. brighteners, perfume and dyes) were used for the washing test:

Storage Stability Test 1:

| Chemical name | Wt. % of active substance in the raw | Wt. % of active substance in the |
|---|---|---|
| Dem ineralized water | 100 | Remainder |
| Alkyl benzene sulfonic acid | 96 | 4.4 |
| Anionic surfactants | 70 | 5.6 |
| C12-C18 fatty acid Na salt | 30 | 2.4 |
| Non-ionic surfactants | 100 | 4.4 |
| Phosphonates | 40 | 0.2 |
| Citric acid | 100 | 1.4 |
| NaOH | 50 | 0.95 |
| Defoamer | t.q. | 0.01 |
| Non-ionic surfactants | 100 | 8-14 |
| Phosphonate | 60 | 0.5-2 |
| Citric acid | 100 | 3-5 |
| NaOH | 50 | 0.5-2 |
| Defoamer | 100 | <1% |
| Glycerol | 99.5 | 1-3 |
| 1,2-propanediol | 100 | 8-12 |
| Monoethanolamine | 100 | 4-8 |
| Soil repellent polymer | 30 | 0.5-1 |

Without opt. brighteners, perfume and enzymes.
Dosage 3.17 g/L

Protease Activity Assays

The activity of the protease is determined by the release of the chromophore para-nitroaniline from the substrate succinyl alanine-alanine-proline-phenylalanine-para-nitroanilide (AAPFpNA; Bachem L-1400). The release of the pNA causes an increase in absorbance at 410 nm, the temporal progression of which is a measure of the enzymatic activity.

The measurement was carried out at a temperature of 25° C., a pH of 8.6, and a wavelength of 410 nm. The measuring time was 5 minutes with a measuring interval of from 20 to 60 seconds.

Measurement approach:
10 µL AAPF solution (70 mg/mL)
1000 µL Tris/HCl (0.1 M, pH 8.6 with 0.1% Brij 35)
10 µL diluted protease solution
Kinetics created over 5 min at 25° C. (410 nm)

Storage Stability Test and Results

The proteases were stirred into a washing agent matrix at the same level of activity and stored at 30° C. By means of a conventional activity assay for proteases (hydrolysis of suc-AAPF-pNA), the starting activity and the residual activity of the protease are measured after 4 weeks' storage at 30° C. In order to generate harsh conditions, the proteases were stored in a washing agent matrix without a stabilizer (boric acid).

The proteases were generated in shake flask supernatants from *Bacillus subtilis*. They were diluted to an equal level of activity. 50% washing agent matrix without boric acid was added to 50% of appropriately diluted *Bacillus subtilis* protease supernatant and mixed well. The sealed glasses were incubated at 30° C. At the time of sampling, a predetermined amount of matrix/protease mixture was removed and dissolved by stirring for 20 min at RT in the sample buffer (0.1 M Tris/HCl, pH 8.6). The AAPF assay is then carried out as described above.

In the first storage stability test, 15 mutants had been found to be advantageous. The activity is shown in % of the residual activity of the starting variants (mutant 1 according to SEQ ID NO:18 or mutant 2 according to SEQ ID NO:2) after 4 weeks' storage at 30° C. Mutants 3-15 relate to starting mutant 1 (SEQ ID NO:18), and mutants 16 and 17 relate to starting mutant 2 (SEQ ID NO:2).

| Variant | SEQ ID NO: | Residual activity |
| --- | --- | --- |
| Mutant 1 | 18 | 100% |
| Mutant 3 | 3 | 153% |
| Mutant 4 | 4 | 148% |
| Mutant 5 | 5 | 150% |
| Mutant 6 | 6 | 133% |
| Mutant 7 | 7 | 154% |
| Mutant 8 | 8 | 132% |
| Mutant 9 | 9 | 147% |
| Mutant 10 | 10 | 146% |
| Mutant 11 | 11 | 132% |
| Mutant 12 | 12 | 144% |
| Mutant 13 | 13 | 136% |
| Mutant 14 | 14 | 138% |
| Mutant 15 | 15 | 132% |
| Mutant 2 | 2 | 100% |
| Mutant 16 | 16 | 121% |
| Mutant 17 | 17 | 110% |

It can be seen that all the mutants exhibit greatly improved stability without the addition of boric acid in comparison with the respective starting mutants according to SEQ ID Nos. 18 and 2. All the mutants exhibit a washing performance that is comparable to the wild type according to SEQ ID NO:1, i.e. they are at most 10% worse in terms of washing performance, which is within the measurement fluctuation (results not shown).

In the second storage stability test, 6 mutants had been found to be advantageous. The activity is shown in % of the residual activity of the starting variant (mutant 18 according to SEQ ID NO:19)—which already has significantly improved stability compared to the wild-type enzyme—after 4 weeks' storage at 30° C.

| Variant | SEQ ID NO: | Residual activity |
| --- | --- | --- |
| Mutant 18 | 19 | 100% |
| Mutant 19 | 20 | 117% |
| Mutant 20 | 21 | 118% |
| Mutant 21 | 22 | 107% |
| Mutant 22 | 23 | 109% |
| Mutant 23 | 24 | 109% |
| Mutant 29 | | 117% |

It can be seen that all the mutants, without the addition of boric acid, exhibit improved stability in comparison with the starting mutant according to SEQ ID NO:19. All the mutants exhibit a washing performance that is comparable to the wild type according to SEQ ID NO:1, i.e. they are at most 10% worse in terms of washing performance, which is within the measurement fluctuation (results not shown).

In another round of testing, additional mutants were tested for stability, with incubation and storage taking place as described above, but at 40° C.

The following mutants have been found to be advantageous. The activity is shown as % of the residual activity with respect to the initial value. The starting variant (mutant 18 according to SEQ ID NO:19) already has markedly improved stability compared to the wild-type enzyme, and was stored for 4 weeks at 40° C.

| Variant | SEQ ID NO: | Residual activity |
| --- | --- | --- |
| Mutant 18 | 19 | 10% |
| Mutant 24 | | 19% |
| Mutant 25 | | 22% |
| Mutant 26 | | 39% |
| Mutant 27 | | 28% |
| Mutant 28 | | 16% |

All the mutants exhibited a further improvement in stability.

The invention claimed is:

1. A protease comprising an amino acid sequence having at least 85% sequence identity with the amino acid sequence given in SEQ ID NO:1 over its entire length and having, in each case based on the numbering according to SEQ ID NO:1, amino acid substitutions which occur:
   (a) at the positions corresponding to positions 9 and 271, and
   (b) at one or more positions corresponding to positions 29, 48, 101, 130, 131, 133, 144, 224, and 252, in each case based on the numbering according to SEQ ID NO:1.

2. The protease according to claim 1, wherein:
   (1) the amino acid substitution at the position 9 is the amino acid substitution 9T, 9H, 9S, or 9A; and wherein the amino acid substitution at the position 271 is Q271E;
   (2) the one or more amino acid substitutions according to (b) is selected from the group consisting of A29G, A48V, D101E, N130D, N130S, N130H, G131D, G131N, G131S, G131K, T133K, T133R, T133Y, N144K, N144L, N144A, S224A, S224T, and N252S, in each case based on the numbering according to SEQ ID NO:1; or
   (3) both.

3. The protease according to claim 1, wherein amino acid substitutions occur:
   (1) at the positions corresponding to positions 9 and 271 and one or more of 130, 131, 133, 144, and 224 in each case based on the numbering according to SEQ ID NO:1, and
   (2) optionally at one or more of the positions corresponding to positions 29, 48, 101, and 252 in each case based on the numbering according to SEQ ID NO:1.

4. The protease according to claim 1, wherein the amino acid substitutions, in each case based on the numbering according to SEQ ID NO:1: occur at P9T, P9H, P9S, or P9A corresponding to position 9 and Q271E corresponding to position 271, optionally S216C corresponding to position 216, as well as additional amino acid substitutions according to one or more of the following:
   (i) N130D, G131S, T133Y, and S224A;
   (ii) N130S, G131S, T133Y, N144L, and S224A;
   (iii) N130D, G131N, T133K, and N144K;
   (iv) N130H, G131N, N144K, and S224A;
   (v) A29G, N130D, G131N, and T133R;
   (vi) A29G, D101E, N130S, G131S, S224T, and N252S;
   (vii) N130H, G131S, and S224A;
   (viii) N130D, G131S, T133K, and S224A;
   (ix) A29G, D101E, N130D, G131K, and S224A;
   (x) N130D, G131N, T133K, N144L, and N252S;
   (xi) G131S, N144K, and S224T;
   (xii) D101E, N130D, G131S, T133Y, N144A, and S224A;
   (xiii) A29G, D101E, N130S, S224T, and N252S;
   (xiv) A48V, G131S, T133R, and S224A; and
   (xv) G131D, T133R, and S224A.

5. The protease according to claim 1, wherein the amino acid substitutions occur, based on the numbering according to SEQ ID NO:1:
   at a further position corresponding to 166 as 166M, 166Q, or 166A; at one or more additional positions corresponding to positions 62, 133, 149, 156, 172, and 217; or both.

6. The protease according to claim 5, wherein the amino acid substitutions at the one or more additional positions corresponding to positions 62, 133, 149, 156, 172, and 217 are selected from the amino acid substitutions 62S, 133R, 133A, 133K, 149I, 156G, 156Q, 172P, 172G, and 217M.

7. The protease according to claim 1, wherein the protease has an amino acid sequence according to one of SEQ ID Nos. 3-17 or 19-23.

8. A protease according to claim 1, further comprising a single or multiple conservative amino acid substitution, wherein the protease comprises:
   (i) the amino acid substitutions P9T, P9H, P9S, or P9A corresponding to position 9 and Q271E corresponding to position 271 based on the numbering according to SEQ ID NO:1, and (ii) one or more of the amino acid substitutions A29G, A48V, D101E, N130D, N130S, N130H, G131S, G131N, G131D, G131K, T133K, T133R, T133Y, N144K, N144L, N144A, S224A, S224T, and N252S at the positions corresponding to positions 29, 48, 101, 130, 131, 133, 144, 224, and 252 based on the numbering according to SEQ ID NO:1.

9. A composition comprising:
at least one protease according to claim 1 and a washing or cleaning agent; and
one or more surfactants.

10. The composition of claim 9, wherein the protease comprises:
   (1) the amino acid substitution at the position 9 is the amino acid substitution 9T, 9H, 9S, or 9A; and wherein the amino acid substitution at the position 271 is Q271E;
   (2) the one or more amino acid substitutions according to (b) is selected from the group consisting of A29G, A48V, D101E, N130D, N130S, N130H, G131D, G131N, G131S, G131K, T133K, T133R, T133Y, N144K,N144L,N144A, S224A, S224T, and N252S, in each case based on the numbering according to SEQ ID NO:1;
   (3) or both.

11. The composition of claim 9, wherein the protease comprises the following amino acid substitutions:
   (1) at the positions corresponding to positions 9 and 271 and one or more of 130, 131, 133, 144, and 224 in each case based on the numbering according to SEQ ID NO:1, and
   (2) optionally at one or more of the positions corresponding to positions 29, 48, 101, and 252 in each case based on the numbering according to SEQ ID NO:1.

12. The composition of claim 9, wherein the protease comprises the following amino acid substitutions, in each case based on the numbering according to SEQ ID NO:1, which occur at P9T, P9H, P9S, or P9A, corresponding to position 9 and Q271E corresponding to position 271, optionally S216C corresponding to position 216, as well as additional amino acid substitutions according to one or more of the following:
   (i) N130D, G131S, T133Y, and S224A;
   (ii) N130S, G131S, T133Y, N144L, and S224A;
   (iii) N130D, G131N, T133K, and N144K;
   (iv) N130H, G131N, N144K, and S224A;
   (v) A29G, N130D, G131N, and T133R;
   (vi) A29G, D101E, N130S, G131S, S224T, and N252S;
   (vii) N130H, G131S, and S224A;
   (viii) N130D, G131S, T133K, and S224A;
   (ix) A29G, D101E, N130D, G131K, and S224A;
   (x) N130D, G131N, T133K, N144L, and N252S;
   (xi) G131S, N144K ,and S224T;
   (xii) D101E, N130D, G131S, T133Y, N144A, and S224A;
   (xiii) A29G, D101E, N130S, S224T, and N252S;
   (xiv) A48V, G131S, T133R, and S224A; and
   (xv) G131D, T133R, and S224A.

13. The composition of claim 9, wherein the amino acid substitutions occur, based on the number according to SEQ ID NO:1:
   (b1) at the position corresponding to 166 as 166M, 166Q, or 166A;
   (b2) at one or more of the positions corresponding to positions 62, 133, 149, 156, 172, and 217;
   (b3) or both.

14. The protease according to claim 1, wherein the protease comprises amino acid substitutions at the positions corresponding to positions 9 and 271, and at one or more of the positions corresponding to positions 29, 48, 131, 133, 144, 224, and 252 in each case based on the numbering according to SEQ ID NO:1.

15. A protease comprising an amino acid sequence having at least 85% sequence identity with the amino acid sequence given in SEQ ID NO:1 over its entire length and having, in each case based on the numbering according to SEQ ID NO:1 amino acid substitutions which occur:
   (a) at the positions corresponding to positions 9, 130, 144, 252, and 271 as the amino acid substitutions 9T, 130D, 144K, 252T, and 271E, and
   (b) optionally at one or more additional positions corresponding to positions 62, 133, 149, 156, 166, 172, and 217 as amino acid substitutions 62S, 133R, 133A, 133K, 149I, 156G, 156Q, 166M, 166Q, 166A, 172P, 172G, and 217M.

* * * * *

SEQUENCE LISTING

<160> NUMBER OF SEQ ID NOS: 24

<210> SEQ ID NO 1
<211> LENGTH: 275

```
<212> TYPE: PRT
<213> ORGANISM: Bacillus pumilus

<400> SEQUENCE: 1

Ala Gln Thr Val Pro Tyr Gly Ile Pro Gln Ile Lys Ala Pro Ala Val
1               5                   10                  15

His Ala Gln Gly Tyr Lys Gly Ala Asn Val Lys Val Ala Val Leu Asp
                20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
    50                  55                  60

Gly Thr His Val Ala Gly Thr Ile Ala Leu Asp Asn Thr Ile Gly
65              70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asn Gly Ser Thr Ala Leu Lys Asn Ala Val Asp Thr Ala Asn Asn
    130                 135                 140

Arg Gly Val Val Val Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Ser Tyr Thr Gly Thr Ser Met Ala Ser
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Gln Ala
            260                 265                 270

Ala Ser Asn
        275

<210> SEQ ID NO 2
<211> LENGTH: 275
<212> TYPE: PRT
<213> ORGANISM: Artificial Sequence
<220> FEATURE:
<223> OTHER INFORMATION: Ausgangsmutante 2

<400> SEQUENCE: 2

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
                20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
```

```
                    50                    55                   60
Gly Thr His Val Ala Gly Thr Ile Ala Ala Leu Asp Asn Thr Ile Gly
 65                  70                   75                   80

Val Leu Gly Val Ala Pro Ser Ala Ser Leu Tyr Ala Val Lys Val Leu
                    85                   90                   95

Asp Arg Asn Gly Asp Gly Gln Tyr Ser Trp Ile Ile Ser Gly Ile Glu
                100                  105                  110

Trp Ala Val Ala Asn Asn Met Asp Val Ile Asn Met Ser Leu Gly Gly
            115                  120                  125

Pro Asn Gly Ser Arg Ala Leu Lys Asn Ala Val Asp Thr Ala Asn Asn
    130                  135                  140

Arg Gly Val Val Val Ala Ala Gly Asn Ser Gly Ser Thr Gly
145                  150                  155                  160

Ser Thr Ser Thr Val Gly Tyr Pro Ala Lys Tyr Asp Ser Thr Ile Ala
                165                  170                  175

Val Ala Asn Val Asn Ser Ser Asn Val Arg Asn Ser Ser Ser Ser Ala
                180                  185                  190

Gly Pro Glu Leu Asp Val Ser Ala Pro Gly Thr Ser Ile Leu Ser Thr
            195                  200                  205

Val Pro Ser Ser Gly Tyr Thr Cys Tyr Thr Gly Thr Ser Met Ala Ala
    210                  215                  220

Pro His Val Ala Gly Ala Ala Leu Ile Leu Ser Lys Asn Pro Asn
225                  230                  235                  240

Leu Ser Asn Ser Gln Val Arg Gln Arg Leu Glu Asn Thr Ala Thr Pro
                245                  250                  255

Leu Gly Asn Ser Phe Tyr Tyr Gly Lys Gly Leu Ile Asn Ala Glu Ala
                260                  265                  270

Ala Ser Asn
        275

<210> SEQ ID NO 3
<211> LENGTH: 275
<212> TYPE: PRT
<213> ORGANISM: Artificial Sequence
<220> FEATURE:
<223> OTHER INFORMATION: Mutationsvariante 1

<400> SEQUENCE: 3

Ala Gln Thr Val Pro Tyr Gly Ile Thr Gln Ile Lys Ala Pro Ala Val
 1                5                   10                   15

His Ala Gln Gly Tyr Lys Gly Ala Asn Val Lys Val Ala Val Leu Asp
                20                   25                   30

Thr Gly Ile His Ala Ala His Pro Asp Leu Asn Val Ala Gly Gly Ala
            35                   40                   45

Ser Phe Val Pro Ser Glu Pro Asn Ala Thr Gln Asp Phe Gln Ser His
 50                  55                   60

Gly Thr His Val Ala Gly Thr Ile Ala Ala Leu Asp Asn Thr Ile Gly
 65                  70                   75                   80

Val Leu Gly Val Ala Pro Ser Ala Ser Leu Tyr Ala Val Lys Val Leu
                85                   90                   95

Asp Arg Asn Gly Asp Gly Gln Tyr Ser Trp Ile Ile Ser Gly Ile Glu
                100                  105                  110

Trp Ala Val Ala Asn Asn Met Asp Val Ile Asn Met Ser Leu Gly Gly
            115                  120                  125

Pro Asp Ser Ser Tyr Ala Leu Lys Asn Ala Val Asp Thr Ala Asn Asn
```

```
                130                 135                 140
Arg Gly Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
                180                 185                 190

Gly Pro Glu Leu Asp Val Ser Ala Pro Gly Thr Ser Ile Leu Ser Thr
                195                 200                 205

Val Pro Ser Ser Gly Tyr Thr Cys Tyr Thr Gly Thr Ser Met Ala Ala
                210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
                260                 265                 270

Ala Ser Asn
        275

<210> SEQ ID NO 4
<211> LENGTH: 275
<212> TYPE: PRT
<213> ORGANISM: Artificial Sequence
<220> FEATURE:
<223> OTHER INFORMATION: Mutationsvariante 2

<400> SEQUENCE: 4

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
                20                  25                  30

Thr Gly Ile His Ala Ala His Pro Asp Leu Asn Val Ala Gly Gly Ala
                35                  40                  45

Ser Phe Val Pro Ser Glu Pro Asn Ala Thr Gln Asp Phe Gln Ser His
        50                  55                  60

Gly Thr His Val Ala Gly Thr Ile Ala Ala Leu Asp Asn Thr Ile Gly
65              70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
                100                 105                 110

Trp Ala Val Ala Asn Asn Met Asp Val Ile Asn Met Ser Leu Gly Gly
                115                 120                 125

Pro Ser Ser Ser Tyr Ala Leu Lys Asn Ala Val Asp Thr Ala Asn Leu
                130                 135                 140

Arg Gly Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
                180                 185                 190

Gly Pro Glu Leu Asp Val Ser Ala Pro Gly Thr Ser Ile Leu Ser Thr
                195                 200                 205

Val Pro Ser Ser Gly Tyr Thr Cys Tyr Thr Gly Thr Ser Met Ala Ala
```

```
            210                 215                 220
Pro His Val Ala Gly Ala Ala Leu Ile Leu Ser Lys Asn Pro Asn
225                 230                 235                 240

Leu Ser Asn Ser Gln Val Arg Gln Leu Glu Asn Thr Ala Thr Pro
                245                 250                 255

Leu Gly Asn Ser Phe Tyr Tyr Gly Lys Gly Leu Ile Asn Ala Glu Ala
                260                 265                 270

Ala Ser Asn
        275

<210> SEQ ID NO 5
<211> LENGTH: 275
<212> TYPE: PRT
<213> ORGANISM: Artificial Sequence
<220> FEATURE:
<223> OTHER INFORMATION: Mutationsvariante 3

<400> SEQUENCE: 5

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
                20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
                100                 105                 110

Trp Ala Val Ala Asn Asn Met Asp Val Ile Asn Met Ser Leu Gly Gly
            115                 120                 125

Pro Asp Asn Ser Lys Ala Leu Lys Asn Ala Val Asp Thr Ala Asn Lys
    130                 135                 140

Arg Gly Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ala
            180                 185                 190

Gly Pro Glu Leu Asp Val Ser Ala Pro Gly Thr Ser Ile Leu Ser Thr
    195                 200                 205

Val Pro Ser Ser Gly Tyr Thr Cys Tyr Thr Gly Thr Ser Met Ala Ser
210                 215                 220

Pro His Val Ala Gly Ala Ala Leu Ile Leu Ser Lys Asn Pro Asn
225                 230                 235                 240

Leu Ser Asn Ser Gln Val Arg Gln Leu Glu Asn Thr Ala Thr Pro
                245                 250                 255

Leu Gly Asn Ser Phe Tyr Tyr Gly Lys Gly Leu Ile Asn Ala Glu Ala
                260                 265                 270

Ala Ser Asn
        275
```

```
<210> SEQ ID NO 6
<211> LENGTH: 275
<212> TYPE: PRT
<213> ORGANISM: Artificial Sequence
<220> FEATURE:
<223> OTHER INFORMATION: Mutationsvariante 4

<400> SEQUENCE: 6

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro His Asn Ser Thr Ala Leu Lys Asn Ala Val Asp Thr Ala Asn Lys
    130                 135                 140

Arg Gly Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Cys Tyr Thr Gly Thr Ser Met Ala Ala
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
            260                 265                 270

Ala Ser Asn
        275

<210> SEQ ID NO 7
<211> LENGTH: 275
<212> TYPE: PRT
<213> ORGANISM: Artificial Sequence
<220> FEATURE:
<223> OTHER INFORMATION: Mutationsvariante 5

<400> SEQUENCE: 7

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Gly Val Leu Asp
            20                  25                  30
```

```
Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asp Asn Ser Arg Ala Leu Lys Asn Ala Val Asp Thr Ala Asn Asn
130                 135                 140

Arg Gly Val Val Val Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Cys Tyr Thr Gly Thr Ser Met Ala Ser
    210                 215                 220

Pro His Val Ala Gly Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
            260                 265                 270

Ala Ser Asn
        275

<210> SEQ ID NO 8
<211> LENGTH: 275
<212> TYPE: PRT
<213> ORGANISM: Artificial Sequence
<220> FEATURE:
<223> OTHER INFORMATION: Mutationsvariante 6

<400> SEQUENCE: 8

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Gly Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Glu Gly Gln Tyr Ser Trp Ile Ile Ser Gly Ile Glu
            100                 105                 110
```

Trp Ala Val Ala Asn Asn Met Asp Val Ile Asn Met Ser Leu Gly Gly
            115                 120                 125

Pro Ser Ser Thr Ala Leu Lys Asn Ala Val Asp Thr Ala Asn Asn
    130                 135                 140

Arg Gly Val Val Val Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ala
            180                 185                 190

Gly Pro Glu Leu Asp Val Ser Ala Pro Gly Thr Ser Ile Leu Ser Thr
            195                 200                 205

Val Pro Ser Ser Gly Tyr Thr Cys Tyr Thr Gly Thr Ser Met Ala Thr
    210                 215                 220

Pro His Val Ala Gly Ala Ala Leu Ile Leu Ser Lys Asn Pro Asn
225                 230                 235                 240

Leu Ser Asn Ser Gln Val Arg Gln Arg Leu Glu Ser Thr Ala Thr Pro
                245                 250                 255

Leu Gly Asn Ser Phe Tyr Tyr Gly Lys Gly Leu Ile Asn Ala Glu Ala
            260                 265                 270

Ala Ser Asn
        275

<210> SEQ ID NO 9
<211> LENGTH: 275
<212> TYPE: PRT
<213> ORGANISM: Artificial Sequence
<220> FEATURE:
<223> OTHER INFORMATION: Mutationsvariante 7

<400> SEQUENCE: 9

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
            115                 120                 125

Pro His Ser Ser Thr Ala Leu Lys Asn Ala Val Asp Thr Ala Asn Asn
    130                 135                 140

Arg Gly Val Val Val Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ala
            180                 185                 190

```
Gly Pro Glu Leu Asp Val Ser Ala Pro Gly Thr Ser Ile Leu Ser Thr
            195                 200                 205

Val Pro Ser Ser Gly Tyr Thr Cys Tyr Thr Gly Thr Ser Met Ala Ala
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
                260                 265                 270

Ala Ser Asn
        275

<210> SEQ ID NO 10
<211> LENGTH: 275
<212> TYPE: PRT
<213> ORGANISM: Artificial Sequence
<220> FEATURE:
<223> OTHER INFORMATION: Mutationsvariante 8

<400> SEQUENCE: 10

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asp Ser Ser Lys Ala Leu Lys Asn Ala Val Asp Thr Ala Asn Asn
    130                 135                 140

Arg Gly Val Val Val Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ala
            180                 185                 190

Gly Pro Glu Leu Asp Val Ser Ala Pro Gly Thr Ser Ile Leu Ser Thr
            195                 200                 205

Val Pro Ser Ser Gly Tyr Thr Cys Tyr Thr Gly Thr Ser Met Ala Ala
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
                260                 265                 270
```

Ala Ser Asn
        275

<210> SEQ ID NO 11
<211> LENGTH: 275
<212> TYPE: PRT
<213> ORGANISM: Artificial Sequence
<220> FEATURE:
<223> OTHER INFORMATION: Mutationsvariante 9

<400> SEQUENCE: 11

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Gly Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Glu Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asp Lys Ser Thr Ala Leu Lys Asn Ala Val Asp Thr Ala Asn Asn
    130                 135                 140

Arg Gly Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Cys Tyr Thr Gly Thr Ser Met Ala Ala
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
            260                 265                 270

Ala Ser Asn
        275

<210> SEQ ID NO 12
<211> LENGTH: 275
<212> TYPE: PRT
<213> ORGANISM: Artificial Sequence
<220> FEATURE:
<223> OTHER INFORMATION: Mutationsvariante 10

<400> SEQUENCE: 12

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asp Asn Ser Lys Ala Leu Lys Asn Ala Val Asp Thr Ala Asn Leu
    130                 135                 140

Arg Gly Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Cys Tyr Thr Gly Thr Ser Met Ala Ser
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Ser Thr Ala Thr Pro
                245                 250                 255

Leu Gly Asn Ser Phe Tyr Tyr Gly Lys Gly Leu Ile Asn Ala Glu Ala
            260                 265                 270

Ala Ser Asn
        275

<210> SEQ ID NO 13
<211> LENGTH: 275
<212> TYPE: PRT
<213> ORGANISM: Artificial Sequence
<220> FEATURE:
<223> OTHER INFORMATION: Mutationsvariante 11

<400> SEQUENCE: 13

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

```
Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asn Ser Ser Thr Ala Leu Lys Asn Ala Val Asp Thr Ala Asn Lys
    130                 135                 140

Arg Gly Val Val Val Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ala
            180                 185                 190

Gly Pro Glu Leu Asp Val Ser Ala Pro Gly Thr Ser Ile Leu Ser Thr
            195                 200                 205

Val Pro Ser Ser Gly Tyr Thr Cys Tyr Thr Gly Thr Ser Met Ala Thr
    210                 215                 220

Pro His Val Ala Gly Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
            260                 265                 270

Ala Ser Asn
        275

<210> SEQ ID NO 14
<211> LENGTH: 275
<212> TYPE: PRT
<213> ORGANISM: Artificial Sequence
<220> FEATURE:
<223> OTHER INFORMATION: Mutationsvariante 12

<400> SEQUENCE: 14

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
                20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Glu Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asp Ser Ser Tyr Ala Leu Lys Asn Ala Val Asp Thr Ala Asn Ala
    130                 135                 140

Arg Gly Val Val Val Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175
```

Val Ala Asn Val Asn Ser Ser Asn Val Arg Asn Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Cys Tyr Thr Gly Thr Ser Met Ala Ala
210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
            245                 250                 255

Leu Gly Asn Ser Phe Tyr Tyr Gly Lys Gly Leu Ile Asn Ala Glu Ala
            260                 265                 270

Ala Ser Asn
        275

<210> SEQ ID NO 15
<211> LENGTH: 275
<212> TYPE: PRT
<213> ORGANISM: Artificial Sequence
<220> FEATURE:
<223> OTHER INFORMATION: Mutationsvariante 13

<400> SEQUENCE: 15

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Gly Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Glu Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Ser Gly Ser Thr Ala Leu Lys Asn Ala Val Asp Thr Ala Asn Asn
130                 135                 140

Arg Gly Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Cys Tyr Thr Gly Thr Ser Met Ala Thr
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Ser Thr Ala Thr Pro
            245                 250                 255

```
Leu Gly Asn Ser Phe Tyr Tyr Gly Lys Gly Leu Ile Asn Ala Glu Ala
            260                 265                 270

Ala Ser Asn
        275

<210> SEQ ID NO 16
<211> LENGTH: 275
<212> TYPE: PRT
<213> ORGANISM: Artificial Sequence
<220> FEATURE:
<223> OTHER INFORMATION: Mutationsvariante 14

<400> SEQUENCE: 16

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Val
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asn Ser Ser Arg Ala Leu Lys Asn Ala Val Asp Thr Ala Asn Asn
    130                 135                 140

Arg Gly Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Cys Tyr Thr Gly Thr Ser Met Ala Ala
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
            260                 265                 270

Ala Ser Asn
        275

<210> SEQ ID NO 17
<211> LENGTH: 275
<212> TYPE: PRT
<213> ORGANISM: Artificial Sequence
<220> FEATURE:
<223> OTHER INFORMATION: Mutationsvariante 15
```

```
<400> SEQUENCE: 17

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asn Asp Ser Arg Ala Leu Lys Asn Ala Val Asp Thr Ala Asn Asn
    130                 135                 140

Arg Gly Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Cys Tyr Thr Gly Thr Ser Met Ala Ala
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
            260                 265                 270

Ala Ser Asn
        275

<210> SEQ ID NO 18
<211> LENGTH: 275
<212> TYPE: PRT
<213> ORGANISM: Artificial Sequence
<220> FEATURE:
<223> OTHER INFORMATION: Ausgangsmuitante 1

<400> SEQUENCE: 18

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
```

```
                65                  70                  75                  80
Val Leu Gly Val Ala Pro Ser Ala Ser Leu Tyr Ala Val Lys Val Leu
                    85                  90                  95

Asp Arg Asn Gly Asp Gly Gln Tyr Ser Trp Ile Ile Ser Gly Ile Glu
                100                 105                 110

Trp Ala Val Ala Asn Asn Met Asp Val Ile Asn Met Ser Leu Gly Gly
            115                 120                 125

Pro Asn Gly Ser Thr Ala Leu Lys Asn Ala Val Asp Thr Ala Asn Asn
    130                 135                 140

Arg Gly Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ala
                180                 185                 190

Gly Pro Glu Leu Asp Val Ser Ala Pro Gly Thr Ser Ile Leu Ser Thr
            195                 200                 205

Val Pro Ser Ser Gly Tyr Thr Cys Tyr Thr Gly Thr Ser Met Ala Ser
    210                 215                 220

Pro His Val Ala Gly Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Glu Ala
            260                 265                 270

Ala Ser Asn
    275

<210> SEQ ID NO 19
<211> LENGTH: 275
<212> TYPE: PRT
<213> ORGANISM: Artificial Sequence
<220> FEATURE:
<223> OTHER INFORMATION: Mutante 18

<400> SEQUENCE: 19

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
                20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
                100                 105                 110

Trp Ala Val Ala Asn Asn Met Asp Val Ile Asn Met Ser Leu Gly Gly
            115                 120                 125

Pro Asp Gly Ser Thr Ala Leu Lys Asn Ala Val Asp Thr Ala Asn Lys
    130                 135                 140

Arg Gly Val Val Val Ala Ala Ala Gly Asn Ser Gly Ser Thr Gly
```

```
            145                 150                 155                 160
    Ser Thr Ser Thr Val Gly Tyr Pro Ala Lys Tyr Asp Ser Thr Ile Ala
                    165                 170                 175

Val Ala Asn Val Asn Ser Ser Asn Val Arg Asn Ser Ser Ser Ser Ala
                    180                 185                 190

Gly Pro Glu Leu Asp Val Ser Ala Pro Gly Thr Ser Ile Leu Ser Thr
                    195                 200                 205

Val Pro Ser Ser Gly Tyr Thr Ser Tyr Thr Gly Thr Ser Met Ala Ser
        210                 215                 220

Pro His Val Ala Gly Ala Ala Ala Leu Ile Leu Ser Lys Asn Pro Asn
    225                 230                 235                 240

Leu Ser Asn Ser Gln Val Arg Gln Arg Leu Glu Thr Thr Ala Thr Pro
                    245                 250                 255

Leu Gly Asn Ser Phe Tyr Tyr Gly Lys Gly Leu Ile Asn Ala Glu Ala
                    260                 265                 270

Ala Ser Asn
            275

<210> SEQ ID NO 20
<211> LENGTH: 275
<212> TYPE: PRT
<213> ORGANISM: Artificial Sequence
<220> FEATURE:
<223> OTHER INFORMATION: Mutante 19

<400> SEQUENCE: 20

Ala Gln Thr Val Pro Tyr Gly Ile Thr Gln Ile Lys Ala Pro Ala Val
    1               5                   10                  15

His Ala Gln Gly Tyr Lys Gly Ala Asn Val Lys Val Ala Val Leu Asp
                    20                  25                  30

Thr Gly Ile His Ala Ala His Pro Asp Leu Asn Val Ala Gly Gly Ala
                    35                  40                  45

Ser Phe Val Pro Ser Glu Pro Asn Ala Thr Gln Asp Phe Gln Ser His
            50                  55                  60

Gly Thr His Val Ala Gly Thr Ile Ala Ala Leu Asp Asn Thr Ile Gly
    65                  70                  75                  80

Val Leu Gly Val Ala Pro Ser Ala Ser Leu Tyr Ala Val Lys Val Leu
                    85                  90                  95

Asp Arg Asn Gly Asp Gly Gln Tyr Ser Trp Ile Ile Ser Gly Ile Glu
                    100                 105                 110

Trp Ala Val Ala Asn Asn Met Asp Val Ile Asn Met Ser Leu Gly Gly
                    115                 120                 125

Pro Asp Gly Ser Thr Ala Leu Lys Asn Ala Val Asp Thr Ala Asn Lys
        130                 135                 140

Arg Gly Val Val Val Ala Ala Ala Gly Asn Ser Gly Ser Thr Gly
    145                 150                 155                 160

Ser Thr Ser Thr Val Met Tyr Pro Ala Lys Tyr Asp Ser Thr Ile Ala
                    165                 170                 175

Val Ala Asn Val Asn Ser Ser Asn Val Arg Asn Ser Ser Ser Ser Ala
                    180                 185                 190

Gly Pro Glu Leu Asp Val Ser Ala Pro Gly Thr Ser Ile Leu Ser Thr
                    195                 200                 205

Val Pro Ser Ser Gly Tyr Thr Ser Tyr Thr Gly Thr Ser Met Ala Ser
        210                 215                 220

Pro His Val Ala Gly Ala Ala Ala Leu Ile Leu Ser Lys Asn Pro Asn
```

```
                225                 230                 235                 240
Leu Ser Asn Ser Gln Val Arg Gln Arg Leu Glu Thr Thr Ala Thr Pro
                    245                 250                 255

Leu Gly Asn Ser Phe Tyr Tyr Gly Lys Gly Leu Ile Asn Ala Glu Ala
                260                 265                 270

Ala Ser Asn
        275

<210> SEQ ID NO 21
<211> LENGTH: 275
<212> TYPE: PRT
<213> ORGANISM: Artificial Sequence
<220> FEATURE:
<223> OTHER INFORMATION: Mutante 20

<400> SEQUENCE: 21

Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
                20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65              70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
                100                 105                 110

Trp Ala Val Ala Asn Asn Met Asp Val Ile Asn Met Ser Leu Gly Gly
            115                 120                 125

Pro Asp Gly Ser Thr Ala Leu Lys Asn Ala Val Asp Thr Ala Asn Lys
    130                 135                 140

Arg Gly Val Val Val Ala Ala Ala Gly Asn Ser Gly Ser Thr Gly
145             150                 155                 160

Ser Thr Ser Thr Val Gln Tyr Pro Ala Lys Tyr Asp Ser Thr Ile Ala
                165                 170                 175

Val Ala Asn Val Asn Ser Ser Asn Val Arg Asn Ser Ser Ser Ser Ala
                180                 185                 190

Gly Pro Glu Leu Asp Val Ser Ala Pro Gly Thr Ser Ile Leu Ser Thr
            195                 200                 205

Val Pro Ser Ser Gly Tyr Thr Ser Tyr Thr Gly Thr Ser Met Ala Ser
    210                 215                 220

Pro His Val Ala Gly Ala Ala Ala Leu Ile Leu Ser Lys Asn Pro Asn
225             230                 235                 240

Leu Ser Asn Ser Gln Val Arg Gln Arg Leu Glu Thr Thr Ala Thr Pro
                245                 250                 255

Leu Gly Asn Ser Phe Tyr Tyr Gly Lys Gly Leu Ile Asn Ala Glu Ala
                260                 265                 270

Ala Ser Asn
        275

<210> SEQ ID NO 22
<211> LENGTH: 275
<212> TYPE: PRT
```

<213> ORGANISM: Artificial Sequence
<220> FEATURE:
<223> OTHER INFORMATION: Mutante 21

<400> SEQUENCE: 22

```
Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asp Gly Ser Thr Ala Leu Lys Asn Ala Val Asp Thr Ala Asn Lys
    130                 135                 140

Arg Gly Val Val Val Val Ala Ala Ala Gly Asn Ser Gly Ser Thr Gly
145                 150                 155                 160

Ser Thr Ser Thr Val Ala Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Ser Tyr Thr Gly Thr Ser Met Ala Ser
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Thr Thr Ala Thr Pro
                245                 250                 255

Leu Gly Asn Ser Phe Tyr Tyr Gly Lys Gly Leu Ile Asn Ala Glu Ala
            260                 265                 270

Ala Ser Asn
        275
```

<210> SEQ ID NO 23
<211> LENGTH: 275
<212> TYPE: PRT
<213> ORGANISM: Artificial Sequence
<220> FEATURE:
<223> OTHER INFORMATION: Mutante 22

<400> SEQUENCE: 23

```
Ala Gln Thr Val Pro Tyr Gly Ile Thr Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45
```

```
Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
 65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
                100                 105                 110

Trp Ala Val Ala Asn Asn Met Asp Val Ile Asn Met Ser Leu Gly Gly
            115                 120                 125

Pro Asp Gly Ser Thr Ala Leu Lys Asn Ala Val Asp Thr Ala Asn Lys
130                 135                 140

Arg Gly Val Val Val Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Ser Met Thr Gly Thr Ser Met Ala Ser
210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Thr Thr Ala Thr Pro
                245                 250                 255

Leu Gly Asn Ser Phe Tyr Tyr Gly Lys Gly Leu Ile Asn Ala Glu Ala
            260                 265                 270

Ala Ser Asn
        275

<210> SEQ ID NO 24
<211> LENGTH: 275
<212> TYPE: PRT
<213> ORGANISM: Artificial Sequence
<220> FEATURE:
<223> OTHER INFORMATION: Mutante 23

<400> SEQUENCE: 24

Ala Gln Thr Val Pro Tyr Gly Ile Thr Gln Ile Lys Ala Pro Ala Val
  1               5                  10                  15

His Ala Gln Gly Tyr Lys Gly Ala Asn Val Lys Val Ala Val Leu Asp
                20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
 65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
                100                 105                 110

Trp Ala Val Ala Asn Asn Met Asp Val Ile Asn Met Ser Leu Gly Gly
            115                 120                 125
```

-continued

```
Pro Asp Gly Ser Thr Ala Leu Lys Asn Ala Val Asp Thr Ala Asn Lys
    130             135             140

Arg Gly Val Val Val Ala Ala Ala Gly Asn Gly Gly Ser Thr Gly
145             150             155             160

Ser Thr Ser Thr Val Gly Tyr Pro Ala Lys Tyr Asp Ser Thr Ile Ala
            165             170             175

Val Ala Asn Val Asn Ser Ser Asn Val Arg Asn Ser Ser Ser Ser Ala
            180             185             190

Gly Pro Glu Leu Asp Val Ser Ala Pro Gly Thr Ser Ile Leu Ser Thr
        195             200             205

Val Pro Ser Ser Gly Tyr Thr Ser Tyr Thr Gly Thr Ser Met Ala Ser
    210             215             220

Pro His Val Ala Gly Ala Ala Ala Leu Ile Leu Ser Lys Asn Pro Asn
225             230             235             240

Leu Ser Asn Ser Gln Val Arg Gln Arg Leu Glu Thr Thr Ala Thr Pro
            245             250             255

Leu Gly Asn Ser Phe Tyr Tyr Gly Lys Gly Leu Ile Asn Ala Glu Ala
            260             265             270

Ala Ser Asn
    275
```